US012741932B2

(12) United States Patent
Backes et al.

(10) Patent No.: US 12,741,932 B2
(45) Date of Patent: Sep. 22, 2026

(54) ISOTOPIC THYROMIMETIC COMPOUNDS

(71) Applicant: Autobahn Therapeutics, Inc., San Diego, CA (US)

(72) Inventors: Bradley Backes, San Francisco, CA (US); Thomas von Geldern, Richmond, IL (US)

(73) Assignee: AUTOBAHN THERAPEUTICS, INC., San Diego, CA (US)

( * ) Notice: Subject to any disclaimer, the term of this patent is extended or adjusted under 35 U.S.C. 154(b) by 825 days.

(21) Appl. No.: 18/000,508

(22) PCT Filed: Jun. 3, 2021

(86) PCT No.: PCT/US2021/035679
§ 371 (c)(1),
(2) Date: Dec. 1, 2022

(87) PCT Pub. No.: WO2021/247847
PCT Pub. Date: Dec. 9, 2021

(65) Prior Publication Data

US 2023/0348364 A1 Nov. 2, 2023

Related U.S. Application Data

(60) Provisional application No. 63/034,328, filed on Jun. 3, 2020.

(51) Int. Cl.
*C07C 235/20* (2006.01)
*A61P 25/28* (2006.01)
*C07C 69/712* (2006.01)

(52) U.S. Cl.
CPC ............ *C07C 235/20* (2013.01); *A61P 25/28* (2018.01); *C07C 69/712* (2013.01)

(58) Field of Classification Search
None
See application file for complete search history.

(56) References Cited

U.S. PATENT DOCUMENTS 3,845,770 A 11/1974 Theeuwes et al.
4,326,525 A 4/1982 Swanson et al.
4,652,441 A 3/1987 Okada et al.
4,675,189 A 6/1987 Kent et al.
4,677,191 A 6/1987 Tanaka et al.
4,723,027 A 2/1988 Stoutamire et al.
4,728,721 A 3/1988 Yamamoto et al.
4,741,897 A 5/1988 Andrews et al.
4,917,893 A 4/1990 Okada et al.
4,992,445 A 2/1991 Lawter et al.
5,001,139 A 3/1991 Lawter et al.
5,023,252 A 6/1991 Hseih
5,466,569 A 11/1995 Eber et al.
5,616,345 A 4/1997 Geoghegan et al.
5,883,294 A 3/1999 Scanlan et al.
6,054,485 A 4/2000 Schwartz et al.
6,107,517 A 8/2000 Scanlan et al.
6,236,946 B1 5/2001 Scanlan et al.
6,441,015 B2 8/2002 Aspnes et al.
6,787,652 B1 9/2004 Dow et al.
7,288,571 B2 10/2007 Hangeland et al.
7,302,347 B2 11/2007 Baxter et al.
7,915,261 B2 3/2011 Ishii et al.
7,919,494 B2 4/2011 Ishii et al.
7,919,495 B2 4/2011 Ishii et al.
9,562,012 B2 2/2017 Tanis et al.
9,701,650 B2 7/2017 Scanlan et al.
10,130,643 B2 11/2018 Cable et al.
10,226,438 B2 3/2019 Scanlan et al.
10,392,356 B2 8/2019 Scanlan et al.
10,544,075 B2 1/2020 Scanlan et al.
10,870,616 B2 12/2020 Scanlan et al.
11,104,654 B2 8/2021 Scanlan et al.
11,325,886 B2 5/2022 Scanlan et al.
11,510,887 B2 11/2022 Scanlan et al.
11,578,032 B2 2/2023 Scanlan
11,613,517 B2 3/2023 Scanlan et al.
11,667,606 B2 6/2023 Von Geldern et al.
11,780,825 B2 10/2023 Zhou et al.
11,827,596 B2 11/2023 Von Geldern et al.
12,466,781 B2 11/2025 Von Geldern et al.
12,528,761 B2 1/2026 Von Geldern et al.
2003/0203898 A1 10/2003 Haning et al.
2003/0215434 A1 11/2003 Khan et al.

(Continued)

FOREIGN PATENT DOCUMENTS

CN 1882327 A 12/2006
CN 101180097 A 5/2008

(Continued)

OTHER PUBLICATIONS

Placzek et.al. (Tetrahedron. Sep. 2, 2015; 71(35): 5946â5951). (Year: 2015).*

Actis et al., Small molecule inhibitors of PCNA/PIP-box interaction suppress translesion DNA synthesis. Bioorg Med Chem. 21(7):1972-1977 (2013).

Alonso-Merino et al., Thyroid hormones inhibit TGF-beta signaling and attenuate fibrotic responses. PNAS USA 113(24):E3451-E3460 (2016).

Ashraf et al., Synthesis, characterization and in vitro hydrolysis studies of ester and amide prodrugs of dexibuprofen. Medicinal Chemistry Research 21:3361-3368 (2012).

Balkwill et al., Smoldering and polarized inflammation in the initiation and promotion of malignant disease. Cancer Cell 7(3):211-217 (2005).

(Continued)

*Primary Examiner* — John S Kenyon
*Assistant Examiner* — Rehana Ismail
(74) *Attorney, Agent, or Firm* — WILSON SONSINI GOODRICH & ROSATI

(57) ABSTRACT

Isotopic compounds are provided that function as thyromimetics, which compounds have utility for treating diseases such as neurodegenerative disorders. Pharmaceutical compositions containing such compounds are also provided, as are methods of their use and preparation.

7 Claims, No Drawings

(56) References Cited

U.S. PATENT DOCUMENTS

| | | | |
|---|---|---|---|
| 2004/0157844 | A1 | 8/2004 | Dow et al. |
| 2005/0282872 | A1 | 12/2005 | Hangeland et al. |
| 2007/0021407 | A1 | 1/2007 | Boyle et al. |
| 2008/0124280 | A1 | 5/2008 | Mousa et al. |
| 2008/0221170 | A1 | 9/2008 | Roberts et al. |
| 2009/0028925 | A1 | 1/2009 | Erion et al. |
| 2009/0062330 | A1 | 3/2009 | Kalafer et al. |
| 2009/0105347 | A1 | 4/2009 | Scanlan et al. |
| 2009/0232879 | A1 | 9/2009 | Cable et al. |
| 2009/0306225 | A1 | 12/2009 | Lichter et al. |
| 2009/0318514 | A1 | 12/2009 | Garcia Collazo et al. |
| 2010/0099608 | A1 | 4/2010 | Browning |
| 2010/0216771 | A1 | 8/2010 | Li |
| 2010/0303934 | A1 | 12/2010 | Soumyanath et al. |
| 2011/0178134 | A1 | 7/2011 | Jaehne et al. |
| 2012/0004166 | A1 | 1/2012 | Keil et al. |
| 2012/0245213 | A1 | 9/2012 | Mosinger et al. |
| 2013/0289024 | A1 | 10/2013 | Johansen et al. |
| 2014/0235676 | A1 | 8/2014 | Landreth |
| 2014/0288077 | A1 | 9/2014 | Fujii et al. |
| 2016/0081955 | A1 | 3/2016 | Scanlan et al. |
| 2016/0199309 | A1 | 7/2016 | Mousa et al. |
| 2016/0244418 | A1 | 8/2016 | Scanlan et al. |
| 2017/0007589 | A1 | 1/2017 | Ding et al. |
| 2017/0226154 | A1 | 8/2017 | Evans et al. |
| 2018/0057472 | A1 | 3/2018 | Scanlan et al. |
| 2019/0175531 | A1 | 6/2019 | Scanlan et al. |
| 2019/0210950 | A1 | 7/2019 | Scanlan et al. |
| 2020/0163930 | A1 | 5/2020 | Jerzak et al. |
| 2020/0181103 | A1 | 6/2020 | Scanlan et al. |
| 2020/0361849 | A1 | 11/2020 | Von Geldern et al. |
| 2020/0405669 | A1 | 12/2020 | Scanlan et al. |
| 2021/0002208 | A1 | 1/2021 | Scanlan |
| 2021/0053917 | A1 | 2/2021 | Von Geldern et al. |
| 2021/0087137 | A1 | 3/2021 | Scanlan et al. |
| 2021/0230146 | A1 | 7/2021 | Zhou et al. |
| 2023/0048992 | A1 | 2/2023 | Von et al. |
| 2023/0242471 | A1 | 8/2023 | Von Geldern et al. |
| 2023/0242473 | A1 | 8/2023 | Von Geldern et al. |
| 2023/0242492 | A1 | 8/2023 | Von Geldern et al. |
| 2024/0425437 | A1 | 12/2024 | Scanlan et al. |

FOREIGN PATENT DOCUMENTS

| | | | | |
|---|---|---|---|---|
| CN | 101189248 | A | 5/2008 | |
| CN | 101547898 | A | 9/2009 | |
| CN | 101600450 | A | 12/2009 | |
| CN | 101610774 | A | 12/2009 | |
| CN | 101848712 | A | 9/2010 | |
| CN | 107848940 | A | 3/2018 | |
| EP | 1148054 | B1 | 11/2005 | |
| EP | 3259246 | A1 | 12/2017 | |
| JP | S59116256 | A | 7/1984 | |
| JP | H09301917 | A | 11/1997 | |
| JP | 2004512303 | A | 4/2004 | |
| JP | 2004517037 | A | 6/2004 | |
| JP | 2008542301 | A | 11/2008 | |
| JP | 2008545711 | A | 12/2008 | |
| JP | 2012106996 | A | 6/2012 | |
| JP | 2016517884 | A | 6/2016 | |
| PE | 20180021 | A1 | 1/2018 | |
| RU | 2007148927 | A | 7/2009 | |
| WO | WO-9321146 | A1 | 10/1993 | |
| WO | WO-9900353 | A1 | 1/1999 | |
| WO | WO-0039077 | A2 | 7/2000 | |
| WO | WO-0073292 | A1 | 12/2000 | |
| WO | WO-0160784 | A1 | 8/2001 | |
| WO | WO-0190053 | A1 | 11/2001 | |
| WO | WO-0200167 | A2 | 1/2002 | |
| WO | WO-0234260 | A1 | 5/2002 | |
| WO | WO-02072539 | A1 | 9/2002 | |
| WO | WO-02081426 | A1 | 10/2002 | |
| WO | WO-2004043939 | A1 | 5/2004 | |
| WO | WO-2006031922 | A2 | 3/2006 | |
| WO | WO-2006128056 | A2 | 11/2006 | |
| WO | WO-2006128058 | A2 | 11/2006 | |
| WO | WO-2007110226 | A1 | 10/2007 | |
| WO | WO-2007132475 | A1 | 11/2007 | |
| WO | WO-2008125724 | A1 | 10/2008 | |
| WO | WO-2013006734 | A1 | 1/2013 | |
| WO | WO-2014078892 | A1 | 5/2014 | |
| WO | WO-2014178892 | A1 | 11/2014 | |
| WO | WO-2014178931 | A1 | 11/2014 | |
| WO | WO-2015188015 | A1 | 12/2015 | |
| WO | WO-2016134292 | A1 | 8/2016 | |
| WO | WO-2017015360 | A1 | 1/2017 | |
| WO | WO-2017201320 | A1 | 11/2017 | |
| WO | WO-2018032012 | A1 | 2/2018 | |
| WO | WO-2018208707 | A1 | 11/2018 | |
| WO | WO-2019160980 | * | 8/2019 | ........... C07C 255/29 |
| WO | WO-2019160980 | A1 | 8/2019 | |
| WO | WO-2020117962 | A1 | 6/2020 | |
| WO | WO-2020118564 | A1 | 6/2020 | |
| WO | WO-2020123861 | A1 | 6/2020 | |
| WO | WO-2020169069 | A1 | 8/2020 | |
| WO | WO-2020180624 | A1 | 9/2020 | |
| WO | WO-2020227549 | A1 | 11/2020 | |
| WO | WO-2021108549 | A1 | 6/2021 | |
| WO | WO-2021247847 | A1 | 12/2021 | |
| WO | WO-2021257804 | A1 | 12/2021 | |
| WO | WO-2021257834 | A1 | 12/2021 | |
| WO | WO-2021257851 | A1 | 12/2021 | |

OTHER PUBLICATIONS

Bastin et al. Salt selection and optimisation procedures for pharmaceutical new chemical entities. Organic Process Research & Development 4(5):427-435 (2000).

Baxi et al., A selective thyroid hormone beta receptor agonist enhances human and rodent oligodendrocyte differentiation. Glia 62(9):1513-1529 (2014).

Baxter et al., Selective activation of thyroid hormone signaling pathways by GC-1: a new approach to controlling cholesterol and body weight. Trends Endocrinol Metab. 15(4):154-157 (2004).

Baxter et al., Selective modulation of thyroid hormone receptor action. J. Steroid Biochem. Mol. Bio. 76:31-42 (2001).

Belikov. Pharmaceutical Chemistry: Manual. Moscow: MEDpress-inform (pp. 27-29) (2007).

Berge et al. Pharmaceutical Salts. Journal of Pharmaceutical Sciences 66(1):1-19 (Jan. 1977).

Berkenstam et al., The thyroid hormone mimetic compound KB2115 lowers plasma LDL cholesterol and stimulates bile acid synthesis without cardiac effects in humans. PNAS USA 105(2):663-667 (2008).

Bernal et al., Action of thyroid hormone in brain. J Endocrinol Invest. 25(3):268-288 (2002).

Bernal et al., Thyroid hormone receptors in brain development and function. Nat Clin Pract Endocrinol Metab. 3(3):249-259 (2007).

Biondi et al., Hypothyroidism as a risk factor for cardiovascular disease. Endocrine 24:1-13 (2004).

Boger et al., Fatty acid amide hydrolase substrate specificity. Bioorg Med Chem Lett. 10(23):2613-2616 (2000).

Borngraeber et al. Ligand Selectivity by Seeking Hydrophobicity in Thyroid Hormone Receptor. PNAS USA 100(26):15358-15363 (2003).

Boymond et al., Preparation of highly functionalized grignard reagents by an iodine-magnesium exchange reaction and its application in solid-phase synthesis. Angew Chem Int Ed Engl. 37(12):1701-1703 (1998).

Calza et al., Thyroid hormone and remyelination in adult central nervous system: a lesson from an inflammatory-demyelinating disease. Brain Res Brain Res Rev. 48(2):339-346 (2005).

Chiellini et al., A high-affinity subtype-selective agonist ligand for the thyroid hormone receptor. Chemistry and Biology 5(6):299-306 (1998).

Chiellini et al., Synthesis and biological activity of novel thyroid hormone analogues: 5'-aryl substituted GC-1 derivatives. Bioorg Med Chem. 10(2):333-346 (2002).

(56) References Cited

OTHER PUBLICATIONS

Cravatt et al., Supersensitivity to anandamide and enhanced endogenous cannabinoid signaling in mice lacking fatty acid amide hydrolase. Proc Natl Acad Sci U S A 98(16):9371-9376 (2001).
Dell'Acqua et al., Functional and molecular evidence of myelin- and neuroprotection by thyroid hormone administration in experimental allergic encephalomyelitis. Neuropathol Appl Neurobiol. 38(5):454-470 (2012).
Devereaux et al., Increasing thyromimetic potency through halogen substitution. ChemMedChem. 11(21):2459-2465 (2016).
D'Intino et al., Triiodothyronine administration ameliorates the demyelination/remyelination ratio in a non-human primate model of multiple sclerosis by correcting tissue hypothyroidism. J Neuroendocrinol. 23(9):778-790 (2011).
Doran et al., The impact of P-glycoprotein on the disposition of drugs targeted for indications of the central nervous system: evaluation using the MDR1A/1B knockout mouse model. Drug Metab Dispos. 33(1):165-174 (2005).
Edgar et al., An efficient and selective method for the preparation of iodophenols. Journal of Organic Chemistry 55:5287-5291 (1990).
Elbers et al. Thyroid Hormone Mimetics: the Past, Current Status and Future Challenges. Cur Atheroscler Rep 18(3):14 (2016).
Engelen et al., X-linked adrenoleukodystrophy (X-ALD): clinical presentation and guidelines for diagnosis, follow-up and management. Orphanet J Rare Dis. 7:51 [1-14] (2012).
Erion et al., Targeting thyroid hormone receptor-beta agonists to the liver reduces cholesterol and triglycerides and improves the therapeutic index. PNAS USA 104(39):15490-15495 (2007).
Ferrara et al., Ester-to-amide rearrangement of ethanolamine-derived prodrugs of sobetirome with increased blood-brain barrier penetration. Bioorg Med Chem. 25(10):2743-2753 (2017).
Fourcade et al., Thyroid hormone induction of the adrenoleukodystrophy-related gene (ABCD2). Mol. Pharmacol. 63:1296-1303 (2003).
Genin et al., Induction of the adrenoleukodystrophy-related gene (ABCD2) by thyromimetics. J Steroid Biochem Mol Biol. 116(1-2):37-43 (2009).
Gold et al. Understanding pathogenesis and therapy of multiple sclerosis via animal models: 70 years of merits and culprits in experimental autoimmune encephalomyelitis research. Brain 129:1953-1971 (2006).
Gould et al. Salt Selection for Basic Drugs. Int J. Pharm. 33:201-217 (1986).
Grover et al., Effects of the thyroid hormone receptor agonist GC-1 on metabolic rate and cholesterol in rats and primates: selective actions relative to 3,5,3'-triiodo-L-thyronine. Endocrinology 145(4):1656-1661 (2004).
Hafer-Macko et al., Immune attack on the Schwann cell surface in acute inflammatory demyelinating polyneuropathy. Ann. Neurol. 39:625-635 (1996).
Hangeland et al., Thyroid receptor ligands. Part 2: Thyromimetics with improved selectivity for the thyroid hormone receptor beta. Bioorg Med Chem Lett 14(13):3549-3553 (2004).
Hartley et al., A thyroid hormone-based strategy for correcting the biochemical abnormality in X-linked adrenoleukodystrophy. Endocrinology 158(5):1328-1338 (2017).
Hashimoto et al., Design and synthesis of complementing ligands for mutant thyroid hormone receptor TRbeta(R320H): a tailor-made approach toward the treatment of resistance to thyroid hormone. Bioorg Med Chem. 13(11):3627-3639 (2005).
Johnson, Demyelinating diseases, in: The Infectious Etiology of Chronic Diseases: Defining the Relationship, Enhancing the Research, and Mitigating the Effects: Workshop Summary. Institute of Medicine (US) Forum on Microbial Threats; Knobler SL, O'Connor S, Lemon SM, et al., editors. Washington (DC): National Academies Press (US); 45-52 (2004).
Jorgensen. Thyroid hormones and analogues. II. Structure-activity relationships. Hormonal Proteins and Peptides; Li, C. H., Ed.; Academic Press: New York 6:107-204 (1978).
Kavirajan et al., Efficacy and adverse effects of cholinesterase inhibitors and memantine in vascular dementia: a meta-analysis of randomised controlled trials. Lancet Neurol. 6(9):782-792 (2007).
Koenning et al., Myelin gene regulatory factor is required for maintenance of myelin and mature oligodendrocyte identity in the adult Cns. J Neurosci. 32(36):12528-12542 (2012).
Krogsgaard-Larsen et al. Chapter 4: Design and application of prodrugs. Textbook of Drug Designing and Discovery, US, Taylor & Francis Inc (3rd Ed.) (pp. P460-P514).
Lee et al., Drug transporters in the central nervous system: brain barriers and brain parenchyma considerations. Pharmacological Review 53(4):569-596 (2001).
Link et al., Photo-caged agonists of the nuclear receptors RARgamma and TRbeta provide unique time-dependent gene expression profiles for light-activated gene patterning. Bioorg Med Chem. 12(22):5949-5959 (2004).
Lu et al., An expedient synthesis of benzyl 2,3,4-tri-O-benzyl-beta-D-glucopyranoside and benzyl 2,3,4-tri-O-benzyl-beta-D-mannopyranoside. Carbohydr Res. 340(6):1213-1217 (2005).
Malm et al., Recent advances in the development of agonists selective for beta1-type thyroid hormone receptor. Mini Rev Med Chem. 7(1):79-86 (2007).
Mandal et al., Pd-C-induced catalytic transfer hydrogenation with triethylsilane. Journal of Organic Chemistry 72(17):6599-6601 (2007).
Martin et al. The proliferating cell nuclear antigen regulates retinoic acid receptor transcriptional activity through direct protein-protein interaction. Nucleic Acids Res. 33(13):4311-21 (2005).
Massague. TGFbeta signalling in context. Nat Rev Mol Cell Biol. 13(10):616-630 (2012).
Meinig et al., Structure-activity relationships of central nervous system penetration by fatty acid amide hydrolase (FAAH)-targeted thyromimetic prodrugs. ACS Med Chem Lett. 10(1):111-116 (2018).
Meinig et al., Targeting fatty-acid amide hydrolase with prodrugs for CNS-selective therapy. ACS Chem Neurosci. 8(11):2468-2476 (2017).
Miller et al., Primary-progressive multiple sclerosis. Lance Neurol. 6:903-912 (2007).
Miyabara et al., Thyroid hormone receptor-beta-selective agonist GC-24 spares skeletal muscle type I to II fiber shift. Cell Tissue Res. 321(2):233-241 (2005).
Montalban et al. Primary progressive multiple sclerosis diagnostic criteria: a reappraisal. Mult Scler 15(12):1459-65 (2009).
Nguyen et al., Hammett analysis of selective thyroid hormone receptor modulators reveals structural and electronic requirements for hormone antagonists. J Am Chem Soc. 127(13):4599-4608 (2005).
Nguyen et al., Rational design and synthesis of a novel thyroid hormone antagonist that blocks coactivator recruitment. J Med Chem. 45(15):3310-3320 (2002).
Ocasio et al., Characterization of thyroid hormone receptor alpha (TRalpha)-specific analogs with varying inner- and outer-ring substituents. Bioorg Med Chem. 16(2):762-770 (2008).
Ocasio et al., Design and characterization of a thyroid hormone receptor alpha (TRalpha)-specific agonist. ACS Chem Biol. 1(9):585-593 (2006).
O'Shea et al., Characterization of skeletal phenotypes of TRalpha1 and TRbeta mutant mice: implications for tissue thyroid status and T3 target gene expression. Nucl Recept Signal 4:e011 [1-5] (2006).
Oppenheimer et al., Molecular basis of thyroid hormone-dependent brain development. Endocrine Reviews 18(4):462-475 (1997).
Patani et al. Bioisosterism: A Rational Approach in Drug Design. Chem. Rev. 96:3147-3176 (1996).
PCT/CN2018/120634 International Search Report and Written Opinion dated Sep. 11, 2019.
PCT/US2016/018732 International Search Report and Written Opinion dated Jun. 1, 2016.
PCT/US2017/033388 International Search Report and Written Opinion dated Aug. 16, 2017.
PCT/US2019/017881 International Search Report and Written Opinion dated May 13, 2019.
PCT/US2019/019576 International Search Report and Written Opinion dated May 13, 2019.

(56) References Cited

OTHER PUBLICATIONS

PCT/US2019/066066 International Search Report and Written Opinion dated Mar. 5, 2020.
PCT/US2020/020199 International Search Report and Written Opinion dated May 14, 2020.
PCT/US2020/062229 International Invitation to Pay Additional Fees dated Jan. 27, 2021.
PCT/US2020/062229 International Search Report and Written Opinion dated Mar. 24, 2021.
PCT/US2021/035679 International Invitation to Pay Additional Fees dated Aug. 16, 2021.
PCT/US2021/035679 International Search Report and Written Opinion dated Oct. 29, 2021.
PCT/US2021/037788 International Invitation to Pay Additional Fees dated Aug. 30, 2021.
PCT/US2021/037788 International Search Report and Written Opinion dated Nov. 10, 2021.
PCT/US2021/037833 International Invitation to Pay Additional Fees dated Aug. 30, 2021.
PCT/US2021/037833 International Search Report and Written Opinion dated Nov. 17, 2021.
PCT/US2021/037862 International Invitation to Pay Additional Fees dated Aug. 30, 2021.
PCT/US2021/037862 International Search Report and Written Opinion dated Nov. 17, 2021.
Penning et al., Structure-activity relationship studies on 1-[2-(4-Phenylphenoxy)ethyl]pyrrolidine (SC-22716), a potent inhibitor of leukotriene A(4) (LTA(4)) hydrolase. Journal of Medicinal Chemistry 43(4):721-735 (2000).
Placzek et al., New synthetic routes to thyroid hormone analogs: d(6)-sobetirome, (3)H-sobetirome, and the antagonist NH-3. Tetrahedron 71(35):5946-5951 (2015).
Placzek et al., Sobetirome prodrug esters with enhanced blood-brain barrier permeability. Bioorg Med Chem. 24(22):5842-5854 (2016).
Pubchem Compound Record for CID 140404356, 2-[3,5-Dichloro-4-[(2-chloro-4-hydroxyphenyl)methyl]phenyl]-4,5-dihydro-1,2,4-triazin-3-one; https://pubchem.ncbi.nlm.nih.gov/compound/140404356 (2019).
Pubchem Compound Record for CID 142030791, 4-[(2,6-Dimethyl-4-pyrrolidin-1-ylphenyl)methyl]-2-propan-2-ylphenol; https://pubchem.ncbi.nlm.nih.gov/compound/142030791 (2019).
PubChem SID 235918886 [ https://pubchem.ncbi.nlm.nih.gov/substance/ 235918886] (2015).
PubChem SID 319635332 [ https://pubchem.ncbi.nlm.nih.gov/substance/319635332 ] (2016).
Pubmed Compound Record for CID 132562601, 2-(4-(3-(1-(2H3)Methyl-(2,2,2-2H3)ethyl)-4-hydroxybenzyl)-3,5-dlmethylphenoxy)acetic acid. U.S. National Library of Medicine https://pubchem.ncbi.nlm.nih.gov/compound/132562601 (2018).
Pubmed Compound Record for CID 132562602, 2-(4-(3-Isopropyl-4-hydroxy(alpha-3H)benzyl)-3,5-dimethylphenoxy)acetic acid. U.S. National Library of Medicine https://pubchem.ncbi.nlm.nih.gov/compound/132562602 (2018).
Reichel et al., The role of blood-brain barrier studies in the pharmaceutical industry. Curr Drug Metab. 7(2):183-203 (2006).
Scanlan. Safety and Pharmacodynamic Study of Sobetirome in X-Linked Adrenoleukodystrophy (X-ALD), available online at ClinicalTrials.gov on Feb. 6, 2013, 3 pages (clinicaltrials.gov/ct2/show/NCT01787578?term=Scanlan&rank=1).
SCANLAN. Sobetirome: a case history of bench-to-clinic drug discovery and development. Heart Fail Rev 15:177-182 (2010).
Shiohara et al., Discovery of novel indane derivatives as liver-selective thyroid hormone receptor beta (TRbeta) agonists for the treatment of dyslipidemia. Bioorg Med Chem 20(11):3622-3634 (2012).
Smith et al., Water soluble prodrug of a COX-2 selective inhibitor suitable for intravenous administration in models of cerebral ischemia. Bioorganic & Medicinal Chemistry Letters 15(13):3197-3200 (2005).
Takahashi et al., Characterisation of liver-specific distribution of a novel 1-benzyl-4-aminoindole-based thyroid hormone receptor beta agonist, SKL-13784: comparison with GC-1. Xenobiotica 46(2):108-116 [1-9] (2016; published online 2015).
Takahashi et al., In vivo evaluation of 1-benzyl-4-aminoindole-based thyroid hormone receptor beta agonists: importance of liver selectivity in drug discovery. Biol Pharm Bull. 37(7):1103-1108 (2014).
Takahashi et al., Synthesis and pharmacological characterization of 1-benzyl-4-aminoindole-based thyroid hormone receptor beta agonists. Bioorg Med Chem. 22(1):488-498 (2014).
Tancevski et al., The resurgence of thyromimetics as lipid-modifying agents. Curr Opin Investig Drugs 10(9):912-918 (2009).
Tangdenpaisal et al., Synthesis of the thyroid hormone analog GC-1 via Bi(OTf)3-catalyzed benzylation. Tetrahedron 70:6789-6795 (2014).
Taub et al., Lipid lowering in healthy volunteers treated with multiple doses of MGL-3196, a liver-targeted thyroid hormone receptor-beta agonist. Atherosclerosis 230(2):373-380 (2013).
Tegeli et al. Synthesis and evaluation of amide prodrugs of mefenamic acid. International Journal of Chemical Sciences 12(3):1033-1043.
THYROID. Abstract from poster presented at the 87th Annual Meeting of the American Thyroid Association (Oct. 18-22, 2017).
Trost et al., The thyroid hormone receptor-beta-selective agonist GC-1 differentially affects plasma lipids and cardiac activity. Endocrinology 141(9):3057-3064 (2000).
U.S. Department of Health and Human Services, Health Resources and Services Administration (HRSA), Orphan Drug Designations and Approvals List as of Sep. 3, 2013. http://www.hrsa.gov/opa/programrequirements/orphandrugsexclusion/ [originally accessed 2014/updated Mar. 1, 2021].
Valadares et al. Role of halogen bonds in thyroid hormone receptor selectivity: pharmacophore-based 3D-QSSR studies. J Chem Inf Model 49(11):2606-2616 (2009).
Varga et al., Antitransforming growth factor-beta therapy in fibrosis: recent progress and implications for systemic sclerosis. Curr Opin Rheumatol. 20(6):720-728 (2008).
Vattakatuchery et al., Acetylcholinesterase inhibitors in cognitive impairment in Huntington's disease: A brief review. 3(3):62-64 (2013).
Ye et al., Thyroid receptor ligands. 1. Agonist ligands selective for the thyroid receptor beta1. J Med Chem. 46(9):1580-1588 (2003).
YEN., Physiological and molecular basis of thyroid hormone action. Physiological Reviews 81(3):1097-1142 (2001).
Yoshihara et al., A designed antagonist of the thyroid hormone receptor. Bioorg Med Chem Lett. 11(21):2821-2825 (2001).
Yoshihara et al., Structural determinants of selective thyromimetics. J Med Chem. 46(14):3152-3161 (2003).
Zhang et al., Thyroid hormone potentially benefits multiple sclerosis via facilitating remyelination. Mol Neurobiol. 53(7):4406-4416 (2016).
Lian, Brian, et al. Compositions comprising thyroid hormone receptor beta (TRB) agonists for the treatment of fibrosis and inflammation: CA Doc No. 173:90753, 1-2 (2020).
Columbano, Amedeo et al. GC-1: A Thyromimetic With Multiple Therapeutic Applications in Liver Disease. Gene Expr. 17(4):265-275 (2017).
PCT/US2017/046807 International Search Report and Written Opinion dated Oct. 19, 2017.
Yen et al., Thyroid hormone action at the cellular, genomic and target gene levels. Mol. Cell Endocrinol. 246:121-127 (2006).

* cited by examiner

ISOTOPIC THYROMIMETIC COMPOUNDS

CROSS-REFERENCE

This application claims benefit of U.S. Provisional Patent Application No. 63/034,328, filed on Jun. 3, 2020, which is incorporated herein by reference in its entirety.

BACKGROUND

Technical Field

The invention relates to isotopic, particularly deuterated, thyromimetic compounds and to products containing the same, as well as to methods of their use and preparation.

Description of the Related Art

Thyroid hormone (TH) is a key signal for oligodendrocyte differentiation and myelin formation during development, and also stimulates remyelination in adult models of multiple sclerosis (MS) (Calzà L et al, *Brain Res Revs* 48:339-346, 2005). However, TH is not an acceptable long-term therapy due to there being virtually no therapeutic window in which remyelination can be achieved while avoiding the cardiotoxicity and bone demineralization associated with chronic hyperthyroidism. Some thyroid hormone analogs can activate thyroid hormone-responsive genes while avoiding the associated downsides of TH by exploiting molecular and physiological features of thyroid hormone receptors (Malm J et al, *Mini Rev Med Chem* 7:79-86, 2007). These receptors are expressed in two major forms with heterogenous tissue distributions and overlapping but distinct sets of target genes (Yen P M, *Physiol Rev* 81:1097-1142, 2001). TRα is enriched in the heart, brain, and bone while TRβ is enriched in the liver (O'Shea P J et al, *Nucl Recept Signal* 4: e011, 2006).

Developing selective thyromimetics has been challenging due to the high sequence homology of thyroid hormone receptor subtypes; namely, only one amino acid residue on the internal surface of the ligand binding domain cavity varies between the α1 and β1 forms. GC-1 was one of the first potent analogs that demonstrated significant TRβ-selectivity in vitro (Chiellini G et al, *Chem Biol* 5:299-306, 1998; Yoshihara H A I et al, *J Med Chem* 46:3152-3161, 2003) and in vivo (Trost S U et al, *Endocrinology* 141:3057-3064, 2000; Grover G J et al, *Endocrinology* 145:1656-1661, 2004; Baxter J D et al, *Trends Endocrinol Metab* 15:154-157, 2004). Advances in the development of thyromimetic compounds include those developed by Tom Scanlan et al. (Oregon Health & Science University) relating to sobetirome and sobetirome analogs as disclosed in WO2014/178892, WO2014/178931, WO2016/134292, WO2017/201320, WO2018/032012, and WO2019/160980.

While progress has been made in this field, there remains a need in the art for further thyromimetic compounds, as well as to products containing the same, and for methods related to their use and preparation.

BRIEF SUMMARY

Disclosed herein are isotopic thyromimetic compounds and products comprising the same, as well as to methods of their use and preparation. In one embodiment, the isotope is deuterium, and deuterated analogs of thyromimetic compounds are provided.

In an embodiment, isotopic thyromimetic compounds are provided of Formula (I):

(I)

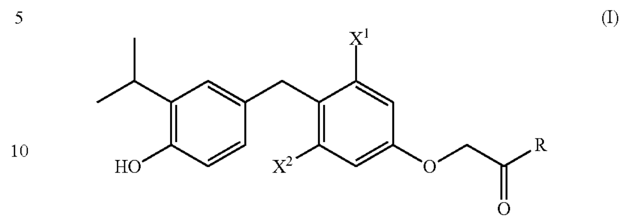

or a pharmaceutically acceptable salt, isomer, racemate, hydrate or solvate thereof, wherein R, $X^1$, and $X^2$ are as defined below, and wherein at least one atom of the compound of Formula (I) is replaced with an isotope thereof. In a more specific embodiment, at least one hydrogen atom of a compound of Formula (I) is replaced with deuterium.

In an embodiment of Formula (I), $X^1$ and $X^2$ are both methyl, R is OH, and isotopic derivatives of sobetirome are provided of Formula (II):

(II)

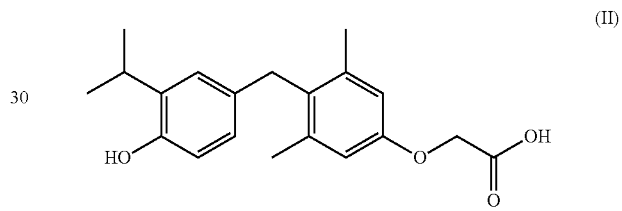

or a pharmaceutically acceptable salt, isomer, racemate, hydrate or solvate thereof, wherein at least one atom of the compound of Formula (II) (i.e., sobetirome) is replaced with an isotope thereof. In a more specific embodiment, at least one hydrogen atom of sobetirome is replaced with deuterium.

In an embodiment of Formula (I), $X^1$ and $X^2$ are both methyl, R is $OR^1$, and isotopic ester derivatives of sobetirome are provided of Formula (III):

(III)

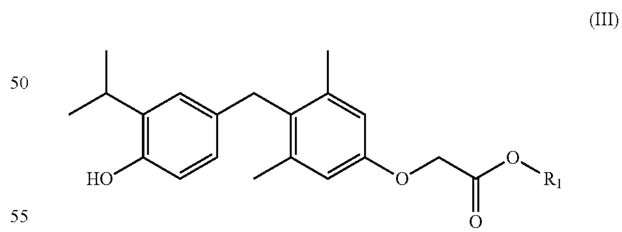

or a pharmaceutically acceptable salt, isomer, racemate, hydrate or solvate thereof, wherein $R^1$ is as defined below, and wherein at least one atom of the compound of Formula (III) is replaced with an isotope thereof. In a more specific embodiment, at least one hydrogen atom of the compound of Formula (III) is replaced with deuterium.

In an embodiment of Formula (I), $X^1$ and $X^2$ are both methyl, R is $NR^2R^3$, and isotopic amide derivatives of sobetirome are provided of Formula (IV):

(IV)

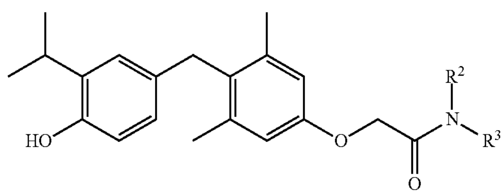

or a pharmaceutically acceptable salt, isomer, racemate, hydrate or solvate thereof, wherein $R^2$ and $R^3$ are as defined below, and wherein at least one atom of the compound of Formula (IV) is replaced with an isotope thereof. In a more specific embodiment, at least one hydrogen atom of the compound of Formula (IV) is replaced with deuterium.

In an embodiment of Formula (I), $X^1$ and $X^2$ are both halo, R is $NR^2R^3$, and isotopic di-halo amide derivatives of sobetirome are provided of Formula (V):

(V)

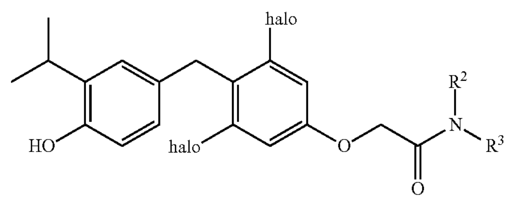

or a pharmaceutically acceptable salt, isomer, racemate, hydrate or solvate thereof, wherein halo, $R^2$ and $R^3$ are as defined below, and wherein at least one atom of the compound of Formula (V) is replaced with an isotope thereof. In a more specific embodiment, at least one hydrogen atom of the compound of Formula (V) is replaced with deuterium.

In an embodiment, a pharmaceutical composition is provided comprising a compound having the structure of any one of Formulas (I)-(VI), or a pharmaceutically acceptable salt, isomer, racemate, hydrate or solvate thereof, in combination with a pharmaceutically acceptable carrier, diluent, or excipient. In some aspects, the pharmaceutical composition is for use in treating a neurodegenerative disorder including neurodegenerative disorders classified as a demyelinating disease such as X-linked adrenoleukodystrophy or multiple sclerosis.

In an embodiment, a method is provided for treating a neurodegenerative disorder in a subject in need thereof, comprising administering a compound having the structure of any one of Formulas (I)-(VI), or a pharmaceutical composition comprising the same. In some aspects, the neurodegenerative disorder can be classified as a demyelinating disease such as X-linked adrenoleukodystrophy or multiple sclerosis.

DETAILED DESCRIPTION

Unless specifically defined otherwise, the technical terms, as used herein, have their normal meaning as understood in the art. The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

As mentioned above, the invention relates to isotopic thyromimetic compounds, to products comprising the same, and to methods for their use and synthesis. The isotopic thyromimetic compounds of Formula (I) (R═OH), Formula (II), or Formula (VI) (R═OH) may bind selectively to a specific TH receptor subtypes; isotopic thyromimetic compounds of Formula (I) (R═$OR^1$), Formula (III), or Formula (VI) (R═$OR^1$) may act as substrates for esterases liberating the isotopic thyromimetic; or isotopic thyromimetic compounds of Formula (I) (R═$NR^2R^3$), Formula (IV) or Formula (V) may act as substrates for the specific hydrolase enzyme fatty acid-amide hydrolase (FAAH) which liberates the isotopic thyromimetic, in which case such conversion may be enhanced in tissues that express high levels of FAAH (such as the central nervous system).

The term "isotopic" as used herein means a compound of any one of Formulas (I)-(VI) wherein one or more atoms of the compound is replaced with an isotope of such one or more atoms. An "isotope", in turn, refers to any of two or more forms of a chemical element, having the same number of protons in the nucleus, but having different numbers of neutrons in the nucleus. For example, an isotopic compound includes a compound in which one or more hydrogen atoms (H) has been replaced with one or more deuterium atoms (D). In this example, deuterium is an isotope of hydrogen, and replacing a hydrogen atom with deuterium (at one or more positions) renders the resulting compound an isotopic compound. For example, and in reference to any one of Formulas (I)-IV), replacing the two methyl groups of the isopropyl moiety ($—CH(CH_3)_2$) with fully deuterated methyl groups ($—CH(CD_3)_2$) would be an isotopic compound of any one of Formulas (I)-(VI). In addition to replacing hydrogen with deuterium, other stable (non-radioactive) isotope substitutions include replacing carbon 12 with carbon 13, while unstable (radioactive) isotopes include replacing hydrogen with tritium, replacing carbon 12 with carbon 14, replacing iodine 127 with iodine 123 or iodine 125, and the like. Accordingly, all reference herein to isotopic compounds of Formulas (I)-(IV), as well as all reference to the more specific embodiments thereof, refers to a compound having one or more isotopic substitutions, including (but not limited to) substitutions of one or more hydrogen atoms with one or more deuterium atoms at any occurrence(s) in the compound.

To this end, the isotopic compounds disclosed herein provide improved advantages relative to their non-isotopic forms. To this end, isotopic modification provides a means of improving existing drugs and/or as a tool in the design of new drugs. For example, isotopic drug design has proven successful in the context of the deuterium (D) kinetic isotope effect. Due to the twofold higher mass of D compared with H, the C-D bond is much more resistant toward oxidative processes (such as its ability to be activated by CYP450 or by other enzymes involved in metabolism), while retaining very similar steric properties. Therefore, H-D isosteric replacement usually retains the pharmacodynamics of the compound, while improving its pharmacokinetics with a repercussion on half-life and/or of area under the curve values and, ultimately, on dose and/or dosing regimen. For example, drug exposure may be enhance with isotopic modification and/or a decrease of clearance. Such benefits are provided to the compounds disclosed hereby by way their isotopic derivation.

In an embodiment, isotopic thyromimetic compounds are provided of Formula (I):

(I)

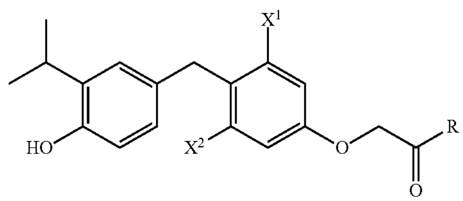

or a pharmaceutically acceptable salt, isomer, racemate, hydrate or solvate thereof, wherein R is OH, $OR^1$ or $NR^2R^3$;

$X^1$ and $X^2$ are both methyl when R is OH, $OR^1$ or $NR^2R^3$, or $X^1$ and $X^2$ are both halo when R is $NR^2R^3$, $R^1$ is alkyl, alkenyl, alkynyl, carbocycle, carbocyclealkyl, heterocycle or heterocyclealkyl, wherein each alkyl, carbocycle, carbocyclealkyl, heterocycle or heterocyclealkyl is optionally substituted with one or more of halo, cyano, $—OR^a$, $—NR^aR^b$, $—S(O)_2R^a$ or $—S(O)_2OR^a$;

$R^2$ and $R^3$ are independently hydrogen, $—OR^a$, $—NR^aR^b$, alkyl, alkenyl, alkynyl, carbocycle, carbocyclealkyl, heterocycle or heterocyclealkyl, wherein each alkyl, carbocycle, carbocyclealkyl, heterocycle or heterocyclealkyl is optionally substituted with one or more of halo, cyano, $—OR^a$, $—NR^aR^b$, $—S(O)_2R^a$ or $—S(O)_2OR^a$;

each occurrence of halo is independently chloro, bromo, fluoro or iodo; and each $R^a$ and $R^b$ is independently hydrogen or alkyl;

and wherein at least one atom of the compound of Formula (I) is replaced with an isotope thereof.

In a more specific embodiment of Formula (I), at least one hydrogen atom is replaced with deuterium. In some embodiments of Formula (I), at least two hydrogen atoms are replaced with deuterium. In some embodiments of Formula (I), at least three hydrogen atoms are replaced with deuterium. In some embodiments of Formula (I), at least four hydrogen atoms are replaced with deuterium. In some embodiments of Formula (I), at least five hydrogen atoms are replaced with deuterium. In some embodiments of Formula (I), at least six hydrogen atoms are replaced with deuterium. In some embodiments of Formula (I), at least seven hydrogen atoms are replaced with deuterium. In some embodiments of Formula (I), at least eight hydrogen atoms are replaced with deuterium. In some embodiments of Formula (I), at least nine hydrogen atoms are replaced with deuterium. In some embodiments of Formula (I), at least ten hydrogen atoms are replaced with deuterium. In some embodiments of Formula (I), at least eleven hydrogen atoms are replaced with deuterium. In some embodiments of Formula (I), at least twelve hydrogen atoms are replaced with deuterium.

As used herein, the term “pharmaceutically acceptable salt” refers to salts prepared by conventional methods. These include basic salts of inorganic and organic acids, such as, without limitation, hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, and mandelic acid. “Pharmaceutically acceptable salts” of the presently disclosed compounds also include those formed from cations such as, without limitation, sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reaction of the free acid with a suitable organic or inorganic base. Any chemical compound recited in this specification may alternatively be administered as a pharmaceutically acceptable salt thereof. Pharmaceutically acceptable salts are also inclusive of the free acid, base, and zwitterionic forms of the disclosed compounds. Descriptions of exemplary pharmaceutically acceptable salts can be found in Stahl and Wermuth, Eds., *Handbook of Pharmaceutical Salts; Properties, Selection and Use*, Wiley VCH (2008). When the compounds disclosed herein include an acidic group such as a carboxy group, then suitable pharmaceutically acceptable cation pairs for the carboxy group are well known to those skilled in the art and include, without limitation, alkaline, alkaline earth, ammonium, and quaternary ammonium cations. Such salts are known to those of skill in the art. Similarly when the compounds disclosed herein include a basic group such as an amino group, then suitable pharmaceutically acceptable anion pairs for the basic group are similarly well known and include halide, hydroxide, perhalate, halite, hypohalite, sulfate, sulfite, phosphate, phosphite, nitrate, nitrite, and others known to those of skill in the art. For additional examples of pharmacologically acceptable salts, see Berge et al, *J. Pharm. Sci.* 66, 1 (1977).

All chiral, diastereomeric, racemic forms of a structure are intended, unless a particular stereochemistry or isomeric form is specifically indicated. Compounds used in the present disclosure can include enriched or resolved optical isomers at any or all asymmetric atoms as are apparent from the depictions, at any degree of enrichment. Both racemic and diastereomeric mixtures, as well as the individual optical isomers can be synthesized so as to be substantially free of their enantiomeric or diastereomeric partners, and these are all within the scope of certain embodiments of the disclosure.

A “hydrate” is a compound that exists in a composition with water molecules. The composition can include water in stoichiometric quantities, such as a monohydrate or a dihydrate, or can include water in random amounts. As the term is used herein a “hydrate” refers to a solid form, i.e., a compound in water solution, while it may be hydrated, is not a hydrate as the term is used herein.

A “solvate” is a similar composition except that a solvent other that water replaces the water. For example, methanol or ethanol can form an “alcoholate”, which can again be stoichiometric or non-stoichiometric. As the term is used herein a “solvate” refers to a solid form, i.e., a compound in solution in a solvent, while it may be solvated, is not a solvate as the term is used herein.

As used herein, the singular terms “a,” “an,” and “the” include plural referents unless context clearly indicates otherwise. Similarly, the word “or” is intended to include “and” unless the context clearly indicates otherwise. Also, as used herein, the term “comprises” means “includes”. Hence “comprising A or B” means including A, B, or A and B.

As used herein, "alkyl" means a straight chain or branched saturated hydrocarbon group. "Lower alkyl" means a straight chain or branched alkyl group having from 1 to 8 carbon atoms, in some embodiments from 1 to 6 carbon atoms, in some embodiments from 1 to 4 carbon atoms, and in some embodiments from 1 to 2 carbon atoms. Examples of straight chain lower alkyl groups include, but are not limited to, methyl, ethyl, n-propyl, n-butyl, n-pentyl, n-hexyl, n-heptyl, and n-octyl groups. Examples of branched lower alkyl groups include, but are not limited to, isopropyl, iso-butyl, sec-butyl, t-butyl, neopentyl, isopentyl, and 2,2-dimethylpropyl groups.

As used herein, "alkenyl" means a straight or branched chain alkyl group as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to $-CH=CH(CH_3)$, $-CH=C(CH_3)_2$, $-C(CH_3)=CH_2$, $-C(CH_3)=CH(CH_3)$, $-C(CH_2CH_3)-CH_2$, vinyl, butadienyl, pentadienyl, and hexadienyl, among others.

As used herein, "alkynyl" means a straight or branched chain alkyl group as defined above, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to $-C\equiv CH$, $-C\equiv C(CH_3)$, $-C\equiv C(CH_2CH_3)$, $-CH_2C\equiv CH$, $-CH_2C\equiv C(CH_3)$, and $-CH_2C\equiv C(CH_2CH_3)$, among others.

The terms "carbocyclic" and "carbocycle" denote a ring structure wherein the atoms of the ring are carbon. Carbocycles may be monocyclic or polycyclic. Carbocycle encompasses both saturated and unsaturated rings. Carbocycle encompasses both cycloalkyl and aryl groups. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N substituents wherein N is the size of the carbocyclic ring with for example, amino, hydroxy, cyano, carboxy, nitro, thio, alkoxy, and halogen groups.

Cycloalkyl groups are alkyl groups forming a ring structure, which can be substituted or unsubstituted. Examples of cycloalkyl include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups.

Aryl groups are cyclic aromatic hydrocarbons that do not contain heteroatoms. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. The phrase "aryl groups" includes groups containing fused rings, such as fused aromatic-aliphatic ring systems (e.g., indanyl, tetrahydronaphthyl, and the like).

As used herein, "carbocyclealkyl" is an alkyl group as defined above in which a hydrogen or carbon bond of the alkyl group is replaced with a bond to a carbocycle group as defined above.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl.

As used herein, "heterocycle" or "heterocyclyl" groups include aromatic and non-aromatic ring compounds (heterocyclic rings) containing 3 or more ring members, of which one or more is a heteroatom such as, but not limited to, N, O, S, or P. A heterocyclyl group as defined herein can be a heteroaryl group or a partially or completely saturated cyclic group including at least one ring heteroatom. In some embodiments, heterocyclyl groups include 3 to 20 ring members, whereas other such groups have 3 to 15 ring members. At least one ring contains a heteroatom, but every ring in a polycyclic system need not contain a heteroatom. For example, a dioxolanyl ring and a benzdioxolanyl ring system (methylenedioxyphenyl ring system) are both heterocyclyl groups within the meaning herein. A heterocyclyl group designated as a C2-heterocyclyl can be a 5-membered ring with two carbon atoms and three heteroatoms, a 6-membered ring with two carbon atoms and four heteroatoms and so forth. Likewise a C4-heterocyclyl can be a 5-membered ring with one heteroatom, a 6-membered ring with two heteroatoms, and so forth. The number of carbon atoms plus the number of heteroatoms sums up to equal the total number of ring atoms. A saturated heterocyclic ring refers to a heterocyclic ring containing no unsaturated carbon atoms.

Heteroaryl groups are aromatic ring compounds containing 5 or more ring members, of which, one or more is a heteroatom such as, but not limited to, N, O, and S. A heteroaryl group designated as a C2-heteroaryl can be a 5-membered ring with two carbon atoms and three heteroatoms, a 6-membered ring with two carbon atoms and four heteroatoms and so forth. Likewise a C4-heteroaryl can be a 5-membered ring with one heteroatom, a 6-membered ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, tetrahydroisoquinolinyl, quinoxalinyl, and quinazolinyl groups. The terms "heteroaryl" and "heteroaryl groups" include fused ring compounds such as wherein at least one ring, but not necessarily all rings, are aromatic, including tetrahydroquinolinyl, tetrahydroisoquinolinyl, indolyl and 2,3-dihydro indolyl.

As used herein, "heterocyclealkyl" is an alkyl group as defined above in which a hydrogen or carbon bond of the alkyl group is replaced with a bond to a heterocycle group as defined above.

As used herein, the term "optionally substituted" refers to a group (e.g., an alkyl, alkenyl, alkynyl, carbocycle, carbocyclealkyl, heterocycle or heterocyclealkyl) having 0, 1, or more substituents, such as 0-25, 0-20, 0-10 or 0-5 substituents. Substituents include, but are not limited to, halo, cyano, —$OR^a$, —$NR^aR^b$, —$S(O)_2R^a$ or —$S(O)_2OR^a$, wherein each $R^a$ and $R^b$ is, independently, H or alkyl.

In an embodiment of Formula (I), $X^1$ and $X^2$ are both methyl, R is OH and isotopic derivatives of sobetirome are provided of Formula (II):

(II)

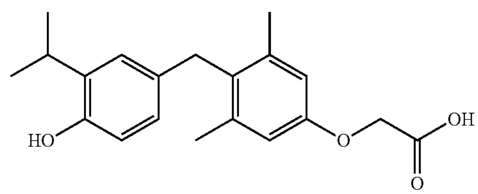

or a pharmaceutically acceptable salt, isomer, racemate, hydrate or solvate thereof, wherein at least one atom of the compound of Formula (II) (i.e., sobetirome) is replaced with an isotope thereof.

In a more specific embodiment of Formula (II), at least one hydrogen atom of sobetirome is replaced with deuterium. In some embodiments of Formula (II), at least two hydrogen atoms of sobetirome are replaced with deuterium. In some embodiments of Formula (II), at least three hydrogen atoms of sobetirome are replaced with deuterium. In some embodiments of Formula (II), at least four hydrogen atoms of sobetirome are replaced with deuterium. In some embodiments of Formula (II), at least five hydrogen atoms of sobetirome are replaced with deuterium. In some embodiments of Formula (II), at least six hydrogen atoms of sobetirome are replaced with deuterium. In some embodiments of Formula (II), at least seven hydrogen atoms of sobetirome are replaced with deuterium. In some embodiments of Formula (II), at least eight hydrogen atoms of sobetirome are replaced with deuterium. In some embodiments of Formula (II), at least nine hydrogen atoms of sobetirome are replaced with deuterium. In some embodiments of Formula (II), at least ten hydrogen atoms of sobetirome are replaced with deuterium. In some embodiments of Formula (II), at least eleven hydrogen atoms of sobetirome are replaced with deuterium. In some embodiments of Formula (II), at least twelve hydrogen atoms of sobetirome are replaced with deuterium.

In a more specific embodiment of Formula (II), the compound is not $d_6$-sobetirome or $^3$H-sobetirome having the following structures (as disclosed in *Tetrahedron* 71 (35): 5946-51, 2015):

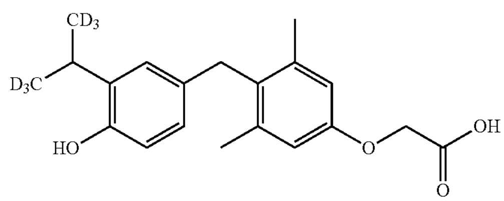

$d_6$-Sobetirome

-continued

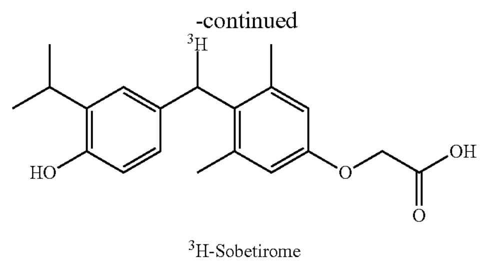

$^3$H-Sobetirome

In an embodiment of Formula (I), $X^1$ and $X^2$ are both methyl, R is $OR^1$ and isotopic ester derivatives of sobetirome are provided of Formula (III):

(III)

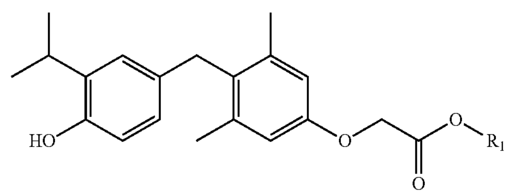

or a pharmaceutically acceptable salt, isomer, racemate, hydrate or solvate thereof, wherein $R^1$ is alkyl, alkenyl, alkynyl, carbocycle, carbocyclealkyl, heterocycle or heterocyclealkyl, wherein each alkyl, carbocycle, carbocyclealkyl, heterocycle or heterocyclealkyl is optionally substituted with one or more of halo, cyano, —$OR^a$, —$NR^aR^b$, —$S(O)_2R^a$ or —$S(O)_2OR^a$; and each $R^a$ and $R^b$ is independently hydrogen or alkyl;

and wherein at least one atom of the compound of Formula (III) is replaced with an isotope thereof.

In a more specific embodiment of Formula (III), at least one hydrogen atom is replaced with deuterium. In some embodiments of Formula (III), at least two hydrogen atoms are replaced with deuterium. In some embodiments of Formula (III), at least three hydrogen atoms are replaced with deuterium. In some embodiments of Formula (III), at least four hydrogen atoms are replaced with deuterium. In some embodiments of Formula (III), at least five hydrogen atoms are replaced with deuterium. In some embodiments of Formula (III), at least six hydrogen atoms are replaced with deuterium. In some embodiments of Formula (III), at least seven hydrogen atoms are replaced with deuterium. In some embodiments of Formula (III), at least eight hydrogen atoms are replaced with deuterium. In some embodiments of Formula (III), at least nine hydrogen atoms are replaced with deuterium. In some embodiments of Formula (III), at least ten hydrogen atoms are replaced with deuterium. In some embodiments of Formula (III), at least eleven hydrogen atoms are replaced with deuterium. In some embodiments of Formula (III), at least twelve hydrogen atoms are replaced with deuterium.

In other embodiments of Formula (III), compounds are provided: where $R^1$ is alkyl; where $R^1$ is saturated alkyl; where $R^1$ is methyl, ethyl, n-propyl, isopropyl, n-butyl, isobutyl, sec-butyl, tert-butyl, n-pentyl, branched pentyl, n-hexyl, or branched hexyl; where $R^1$ is methyl; where $R^1$ is unsaturated alkyl; where $R^1$ is ethenyl, ethynyl, propenyl, or propynyl; or where $R^1$ is alkyl substituted with one or more of halo, cyano, —$OR^a$, —$NR^aR^b$, —$S(O)_2R^a$, or —$S(O)_2OR^a$ and each $R^a$ and $R^b$ is independently hydrogen or alkyl.

In other embodiments of Formula (III), compounds are provided: where $R^1$ is carbocycle or carbocyclealkyl, each of which is optionally substituted with one or more of halo, cyano, —$OR^a$, —$NR^aR^b$, —$S(O)_2R^a$ or —$S(O)_2OR^a$, where $R^1$ is cycloalkyl optionally substituted with one or more of halo, cyano, —$OR^a$, —$NR^aR^b$, —$S(O)_2R^a$ or —$S(O)_2OR^a$; wherein $R^1$ is aryl optionally substituted with one or more of halo, cyano, —$OR^a$, —$NR^aR^b$, —$S(O)_2R^a$ or —$S(O)_2OR^a$; and where $R^1$ is carbocyclealkyl optionally substituted with one or more of halo, cyano, —$OR^a$, —$NR^aR^b$, —$S(O)_2R^a$ or —$S(O)_2OR^a$ and each $R^a$ and $R^b$ is independently hydrogen or alkyl.

In other embodiments of Formula (III), compounds are provided where $R^1$ is heterocycle or heterocyclealkyl, each of which is optionally substituted with one or more of halo, cyano, —$OR^a$, —$NR^aR^b$, —$S(O)_2R^a$ or —$S(O)_2OR^a$, and each $R^a$ and $R^b$ is independently hydrogen or alkyl.

In an embodiment of Formula (I), $X^1$ and $X^2$ are both methyl, R is $NR^2R^3$, and isotopic amide derivatives of sobetirome are provided of Formula (IV):

(IV)

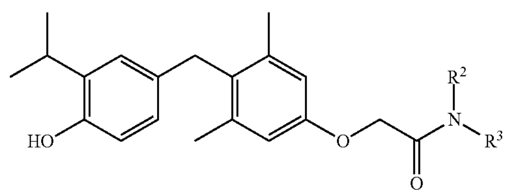

or a pharmaceutically acceptable salt, isomer, racemate, hydrate or solvate thereof, wherein:

$X^1$ and $X^2$ are independently chlorine, bromine, fluorine or iodine;

$R^2$ and $R^3$ are independently hydrogen, —$OR^a$, —$NR^aR^b$, alkyl, alkenyl, alkynyl, carbocycle, carbocyclealkyl, heterocycle or heterocyclealkyl, wherein each alkyl, carbocycle, carbocyclealkyl, heterocycle or heterocyclealkyl is optionally substituted with one or more of halo, cyano, —$OR^a$, —$NR^aR^b$, —$S(O)_2R^a$ or —$S(O)_2OR^a$; and each $R^a$ and $R^b$ is independently hydrogen or alkyl;

and wherein at least one atom of the compound of Formula (IV) is replaced with an isotope thereof.

In a more specific embodiment of Formula (IV), at least one hydrogen atom is replaced with deuterium. In some embodiments of Formula (IV), at least two hydrogen atoms are replaced with deuterium. In some embodiments of Formula (IV), at least three hydrogen atoms are replaced with deuterium. In some embodiments of Formula (IV), at least four hydrogen atoms are replaced with deuterium. In some embodiments of Formula (IV), at least five hydrogen atoms are replaced with deuterium. In some embodiments of Formula (IV), at least six hydrogen atoms are replaced with deuterium. In some embodiments of Formula (IV), at least seven hydrogen atoms are replaced with deuterium. In some embodiments of Formula (IV), at least eight hydrogen atoms are replaced with deuterium. In some embodiments of Formula (IV), at least nine hydrogen atoms are replaced with deuterium. In some embodiments of Formula (IV), at least ten hydrogen atoms are replaced with deuterium. In some embodiments of Formula (IV), at least eleven hydrogen atoms are replaced with deuterium. In some embodiments of Formula (IV), at least twelve hydrogen atoms are replaced with deuterium.

In other embodiments of Formula (IV), compounds are provided: where $R^2$ is hydrogen; where $R^2$ is —$OR^a$ and $R^a$ is hydrogen or alkyl; where $R^2$ is —OH or —OMe; where $R^2$ is —$NR^aR^b$ and each $R^a$ and $R^b$ is independently hydrogen or alkyl; or where $R^2$ is —$NH_2$.

In other embodiments of Formula (IV), compounds are provide: wherein $R^2$ is alkyl; where $R^2$ is saturated alkyl; where $R^2$ is methyl, ethyl, n-propyl, isopropyl, n-butyl, isobutyl, sec-butyl, tert-butyl, n-pentyl, branched pentyl, n-hexyl, or branched hexyl; where $R^2$ is methyl; where $R^2$ is unsaturated alkyl; where $R^2$ is ethenyl, ethynyl, propenyl, or propynyl; or where $R^2$ is alkyl substituted with one or more of halo, cyano, —$OR^a$, —$NR^aR^b$, —$S(O)_2R^a$, or —$S(O)_2OR^a$ and each $R^a$ and $R^b$ is independently hydrogen or alkyl.

In other embodiments of Formula (IV), compounds are provided: where $R^2$ is carbocycle or carbocyclealkyl, each of which is optionally substituted with one or more of halo, cyano, —$OR^a$, —$NR^aR^b$, —$S(O)_2R^a$ or —$S(O)_2OR^a$; where $R^2$ is cycloalkyl optionally substituted with one or more of halo, cyano, —$OR^a$, —$NR^aR^b$, —$S(O)_2R^a$ or —$S(O)_2OR^a$; wherein $R^2$ is aryl optionally substituted with one or more of halo, cyano, —$OR^a$, —$NR^aR^b$, —$S(O)_2R^a$ or —$S(O)_2OR^a$; or where $R^2$ is carbocyclealkyl optionally substituted with one or more of halo, cyano, —$OR^a$, —$NR^aR^b$, —$S(O)_2R^a$ or —$S(O)_2OR^a$ and each $R^a$ and $R^b$ is independently hydrogen or alkyl.

In another embodiment of Formula (IV), compounds are provided where $R^2$ is heterocycle or heterocyclealkyl, each of which is optionally substituted with one or more of halo, cyano, —$OR^a$, —$NR^aR^b$, —$S(O)_2R^a$ or —$S(O)_2OR^a$, and each $R^a$ and $R^b$ is independently hydrogen or alkyl.

In another embodiment of Formula (IV), compounds are provided where $R^2$ is hydrogen.

In another embodiment of Formula (IV), compounds are provided where $R^3$ is hydrogen.

In another embodiment of Formula (IV), compounds are provided where $R^2$ and $R^3$ are alkyl; or where $R^2$ and $R^3$ are both methyl. In another embodiment of Formula (IV), compounds are provided where $R^2$ is methyl and $R^3$ is hydrogen. In another embodiment of Formula (IV), compounds are provided where $R^2$ and $R^3$ are both hydrogen.

In an embodiment of Formula (I), $X^1$ and $X^2$ are both halo, R is $NR^2R^3$, and isotopic di-halo amide derivatives of sobetirome are provided of Formula (V):

(V)

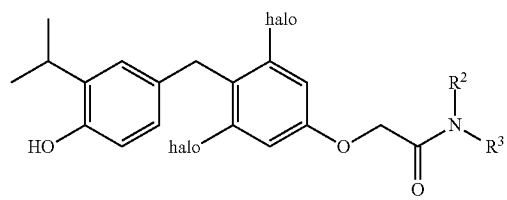

or a pharmaceutically acceptable salt, isomer, racemate, hydrate or solvate thereof, wherein $R^2$ and $R^3$ are independently hydrogen, —$OR^a$, —$NR^aR^b$, alkyl, alkenyl, alkynyl, carbocycle, carbocyclealkyl, heterocycle or heterocyclealkyl, wherein each alkyl, carbocycle, carbocyclealkyl, heterocycle or heterocyclealkyl is optionally substituted with one or more of halo, cyano, —$OR^a$, —$NR^aR^b$, —$S(O)_2R^a$ or —$S(O)_2OR^a$;

each occurrence of halo is independently chloro, bromo, fluoro or iodo; and each $R^a$ and $R^b$ is independently hydrogen or alkyl;

and wherein at least one atom of the compound of Formula (V) is replaced with an isotope thereof.

In a more specific embodiment of Formula (V), at least one hydrogen atom is replaced with deuterium. In some embodiments of Formula (V), at least two hydrogen atoms are replaced with deuterium. In some embodiments of Formula (V), at least three hydrogen atoms are replaced with deuterium. In some embodiments of Formula (V), at least four hydrogen atoms are replaced with deuterium. In some embodiments of Formula (V), at least five hydrogen atoms are replaced with deuterium. In some embodiments of Formula (V), at least six hydrogen atoms are replaced with deuterium. In some embodiments of Formula (V), at least seven hydrogen atoms are replaced with deuterium. In some embodiments of Formula (V), at least eight hydrogen atoms are replaced with deuterium. In some embodiments of Formula (V), at least nine hydrogen atoms are replaced with deuterium. In some embodiments of Formula (V), at least ten hydrogen atoms are replaced with deuterium. In some embodiments of Formula (V), at least eleven hydrogen atoms are replaced with deuterium. In some embodiments of Formula (V), at least twelve hydrogen atoms are replaced with deuterium.

In a more specific embodiment of Formula (V), each occurrence of halo on the phenyl ring is independently chloro or bromo.

In a more specific embodiments of Formula (V), both occurrences of halo on the phenyl ring are chloro, or both occurrences of halo on the phenyl ring are bromine, or one occurrence of halo on the phenyl ring is chloro and the other occurrence of halo on the phenyl ring is bromo.

In other embodiments of Formula (V), compounds are provided: where $R^2$ is hydrogen; where $R^2$ is —$OR^a$ and $R^a$ is hydrogen or alkyl; where $R^2$ is —OH or —OMe; where $R^2$ is —$NR^aR^b$ and each $R^a$ and $R^b$ is independently hydrogen or alkyl; or where $R^2$ is —$NH_2$.

In other embodiments of Formula (V), compounds are provide: wherein $R^2$ is alkyl; where $R^2$ is saturated alkyl; where $R^2$ is methyl, ethyl, n-propyl, isopropyl, n-butyl, isobutyl, sec-butyl, tert-butyl, n-pentyl, branched pentyl, n-hexyl, or branched hexyl; where $R^2$ is methyl; where $R^2$ is unsaturated alkyl; where $R^2$ is ethenyl, ethynyl, propenyl, or propynyl; or where $R^2$ is alkyl substituted with one or more of halo, cyano, —$OR^a$, —$NR^aR^b$, —$S(O)_2R^a$, or —$S(O)_2OR^a$ and each $R^a$ and $R^b$ is independently hydrogen or alkyl.

In other embodiments of Formula (V), compounds are provided: where $R^2$ is carbocycle or carbocyclealkyl, each of which is optionally substituted with one or more of halo, cyano, —$OR^a$, —$NR^aR^b$, —$S(O)_2R^a$ or —$S(O)_2OR^a$; where $R^2$ is cycloalkyl optionally substituted with one or more of halo, cyano, —$OR^a$, —$NR^aR^b$, —$S(O)_2R^a$ or —$S(O)_2OR^a$; wherein $R^2$ is aryl optionally substituted with one or more of halo, cyano, —$OR^a$, —$NR^aR^b$, —$S(O)_2R^a$ or —$S(O)_2OR^a$; or where $R^2$ is carbocyclealkyl optionally substituted with one or more of halo, cyano, —$OR^a$, —$NR^aR^b$, —$S(O)_2R^a$ or —$S(O)_2OR^a$ and each $R^a$ and $R^b$ is independently hydrogen or alkyl.

In another embodiment of Formula (V), compounds are provided where $R^2$ is heterocycle or heterocyclealkyl, each of which is optionally substituted with one or more of halo, cyano, —$OR^a$, —$NR^aR^b$, —$S(O)_2R^a$ or —$S(O)_2OR^a$, and each $R^a$ and $R^b$ is independently hydrogen or alkyl.

In another embodiment of Formula (V), compounds are provided where $R^2$ is hydrogen.

In another embodiment of Formula (V), compounds are provided where $R^3$ is hydrogen.

In another embodiment of Formula (V), compounds are provided where $R^2$ and $R^3$ are alkyl; or where $R^2$ and $R^3$ are both methyl. In another embodiment of Formula (V), compounds are provided where $R^2$ is methyl and $R^3$ is hydrogen. In another embodiment of Formula (V), compounds are provided where $R^2$ and $R^3$ are both hydrogen.

In another embodiment, isotopic thyromimetic compounds are provided of Formula (VI):

(VI)

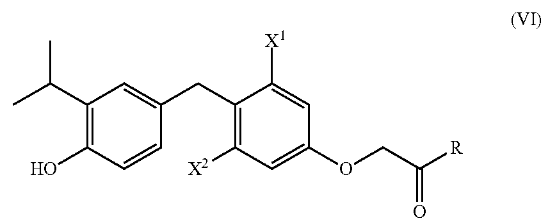

or a pharmaceutically acceptable salt, isomer, racemate, hydrate or solvate thereof, wherein R is OH or $OR^1$;

$X^1$ and $X^2$ are each independently halo;

$R^1$ is alkyl, alkenyl, alkynyl, carbocycle, carbocyclealkyl, heterocycle or heterocyclealkyl, wherein each alkyl, carbocycle, carbocyclealkyl, heterocycle or heterocyclealkyl is optionally substituted with one or more of halo, cyano, —$OR^a$, —$NR^aR^b$, —$S(O)_2R^a$ or —$S(O)_2OR^a$;

$R^2$ and $R^3$ are independently hydrogen, —$OR^a$, —$NR^aR^b$, alkyl, alkenyl, alkynyl, carbocycle, carbocyclealkyl, heterocycle or heterocyclealkyl, wherein each alkyl, carbocycle, carbocyclealkyl, heterocycle or heterocyclealkyl is optionally substituted with one or more of halo, cyano, —$OR^a$, —$NR^aR^b$, —$S(O)_2R^a$ or —$S(O)_2OR^a$;

each occurrence of halo is independently chloro, bromo, fluoro or iodo; and each $R^a$ and $R^b$ is independently hydrogen or alkyl;

and wherein at least one atom of the compound of Formula (I) is replaced with an isotope thereof.

In a more specific embodiment of Formula (VI), at least one hydrogen atom is replaced with deuterium. In some embodiments of Formula (VI), at least two hydrogen atoms are replaced with deuterium. In some embodiments of Formula (VI), at least three hydrogen atoms are replaced with deuterium. In some embodiments of Formula (VI), at least four hydrogen atoms are replaced with deuterium. In some embodiments of Formula (VI), at least five hydrogen atoms are replaced with deuterium. In some embodiments of Formula (VI), at least six hydrogen atoms are replaced with deuterium. In some embodiments of Formula (VI), at least seven hydrogen atoms are replaced with deuterium. In some embodiments of Formula (VI), at least eight hydrogen atoms are replaced with deuterium. In some embodiments of Formula (VI), at least nine hydrogen atoms are replaced with deuterium. In some embodiments of Formula (VI), at least ten hydrogen atoms are replaced with deuterium. In some embodiments of Formula (VI), at least eleven hydrogen atoms are replaced with deuterium. In some embodiments of Formula (VI), at least twelve hydrogen atoms are replaced with deuterium.

In some embodiments of Formula (VI), $X^1$ and $X^2$ are each chloro. In some embodiments of Formula (VI), $X^1$ and $X^2$ are each bromo. In some embodiments of Formula (VI), $X^1$ is chloro and $X^2$ is bromo.

In some embodiments of Formula (VI), R is OH.

In some embodiments of Formula (VI), R is $OR^1$.

Representative compounds of Formula (I), as well as Formulas (II)-(VI) as applicable, include the compounds listed in Table 1.

TABLE 1

| Representative Compounds | |
|---|---|
| Cpd. No. | Structure |
| A-15 | 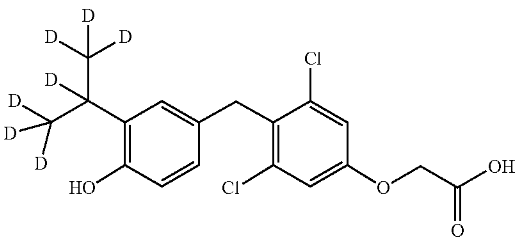 [SMILES: [2H]C([2H])([2H])C([2H])(c1cc(Cc2c(Cl)cc(OCC(=O)O)cc2Cl)ccc1O)C([2H])([2H])[2H]] |
| 1 | 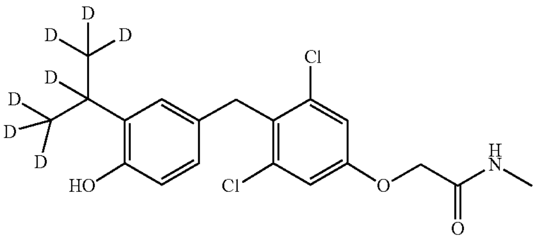 [SMILES: [2H]C([2H])([2H])C([2H])(c1cc(Cc2c(Cl)cc(OCC(=O)NC)cc2Cl)ccc1O)C([2H])([2H])[2H]] |
| 2 | 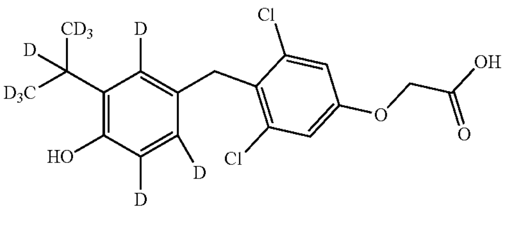 [SMILES: [2H]c1c([2H])c(Cc2c(Cl)cc(OCC(=O)O)cc2Cl)c([2H])c(C([2H])(C([2H])([2H])[2H])C([2H])([2H])[2H])c1O] |
| 3 | 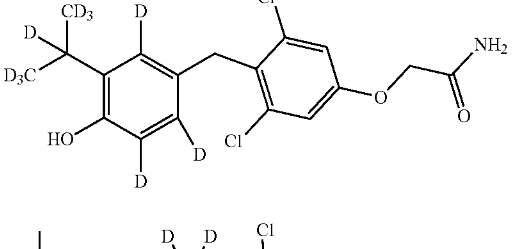 |
| 4 | 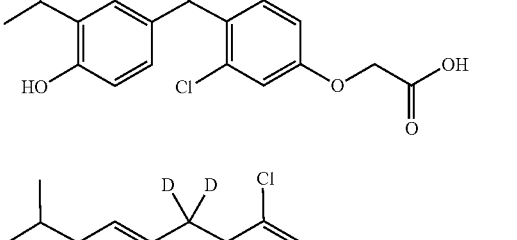 |
| 5 | 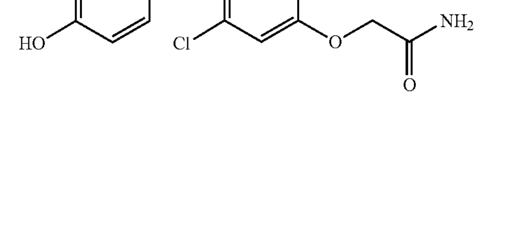 |

TABLE 1-continued
| Representative Compounds | |
|---|---|
| Cpd. No. | Structure |
| 6 | 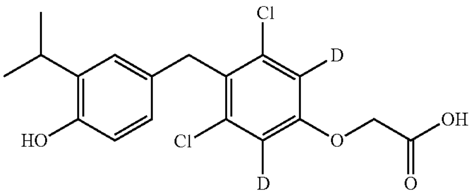 [SMILES: [2H]c1c(Cl)c(Cc2ccc(O)c(C(C)C)c2)c(Cl)c([2H])c1OCC(=O)O] |
| 7 | 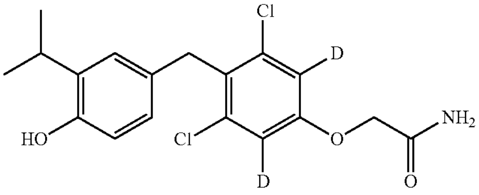 [SMILES: [2H]c1c(Cl)c(Cc2ccc(O)c(C(C)C)c2)c(Cl)c([2H])c1OCC(N)=O] |
| 8 | 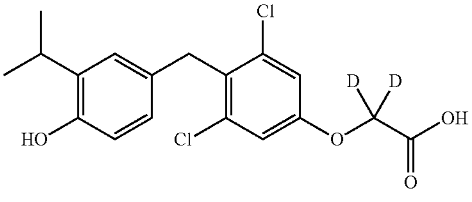 [SMILES: [2H]C([2H])(Oc1cc(Cl)c(Cc2ccc(O)c(C(C)C)c2)c(Cl)c1)C(=O)O] |
| 9 | 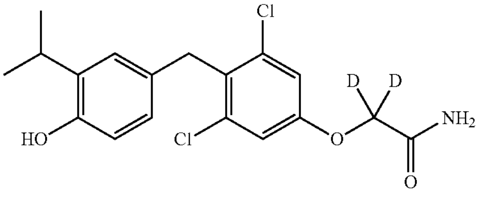 [SMILES: [2H]C([2H])(Oc1cc(Cl)c(Cc2ccc(O)c(C(C)C)c2)c(Cl)c1)C(N)=O] |
| 10 | 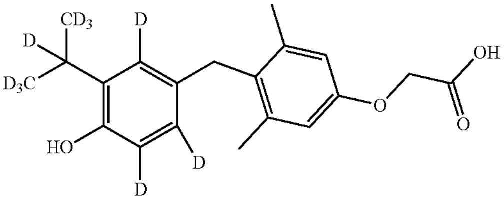 [SMILES: [2H]c1c([2H])c(Cc2c(C)cc(OCC(=O)O)cc2C)c([2H])c(C([2H])(C([2H])([2H])[2H])C([2H])([2H])[2H])c1O] |
| 11 | 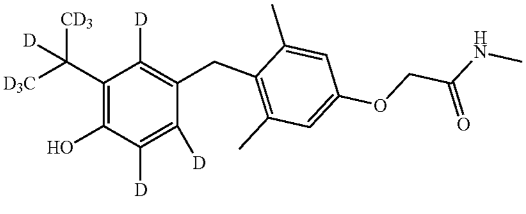 [SMILES: [2H]c1c([2H])c(Cc2c(C)cc(OCC(=O)NC)cc2C)c([2H])c(C([2H])(C([2H])([2H])[2H])C([2H])([2H])[2H])c1O] |
| 12 | 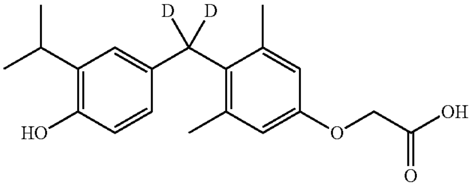 [SMILES: [2H]C([2H])(c1ccc(O)c(C(C)C)c1)c1c(C)cc(OCC(=O)O)cc1C] |

TABLE 1-continued
| Representative Compounds | |
|---|---|
| Cpd. No. | Structure |
| 13 | 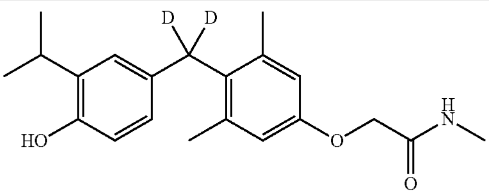 [SMILES: [2H]C([2H])(c1ccc(O)c(C(C)C)c1)c1c(C)cc(OCC(=O)NC)cc1C] |
| 14 | 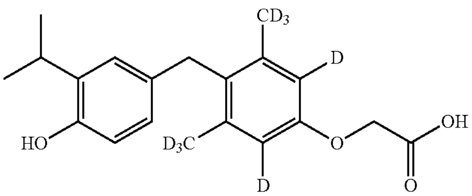 [SMILES: [2H]c1c(OCC(=O)O)c([2H])c(C([2H])([2H])[2H])c(Cc2ccc(O)c(C(C)C)c2)c1C([2H])([2H])[2H]] |
| 15 | 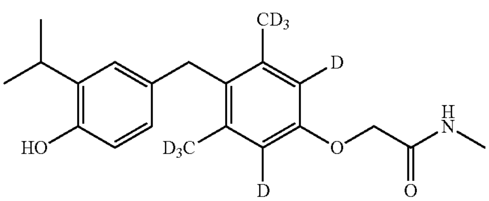 [SMILES: [2H]c1c(OCC(=O)NC)c([2H])c(C([2H])([2H])[2H])c(Cc2ccc(O)c(C(C)C)c2)c1C([2H])([2H])[2H]] |
| 16 | 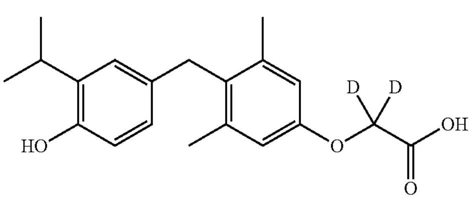 [SMILES: [2H]C([2H])(Oc1cc(C)c(Cc2ccc(O)c(C(C)C)c2)c(C)c1)C(=O)O] |
| 17 | 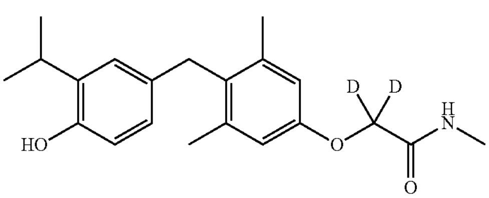 [SMILES: [2H]C([2H])(Oc1cc(C)c(Cc2ccc(O)c(C(C)C)c2)c(C)c1)C(=O)NC] |
| 18 | 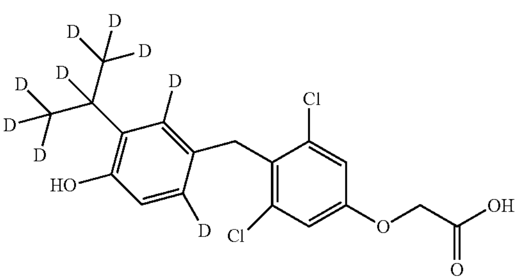 [SMILES: [2H]c1cc(O)c(C([2H])(C([2H])([2H])[2H])C([2H])([2H])[2H])c([2H])c1Cc1c(Cl)cc(OCC(=O)O)cc1Cl] |
| 19 | 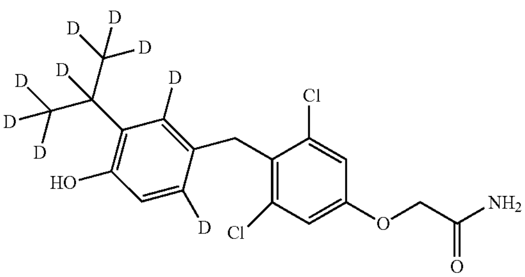 [SMILES: [2H]c1cc(O)c(C([2H])(C([2H])([2H])[2H])C([2H])([2H])[2H])c([2H])c1Cc1c(Cl)cc(OCC(N)=O)cc1Cl] |

TABLE 1-continued

| Representative Compounds | |
|---|---|
| Cpd. No. | Structure |
| 20 | 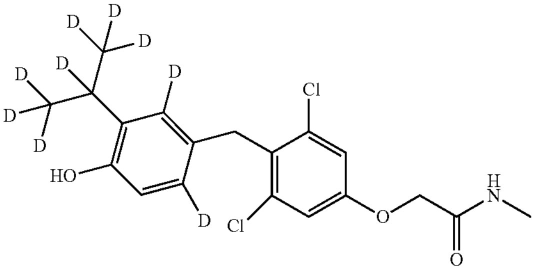 [SMILES: [2H]c1cc(O)c(C([2H])(C([2H])([2H])[2H])C([2H])([2H])[2H])c([2H])c1Cc1c(Cl)cc(OCC(=O)NC)cc1Cl] |

In certain embodiments, the invention provides a pharmaceutical composition comprising a compound of any one of Formulas (I)-(VI) (the "active" compound) together with at least one pharmaceutically acceptable carrier, diluent, or excipient. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid, or lower alkyl ethers of cellulose, silicic acid, fatty acids, fatty acid amines, fatty acid monoglycerides and diglycerides, pentaerythritol fatty acid esters, polyoxyethylene, hydroxymethylcellulose, and polyvinylpyrrolidone. Similarly, the carrier or diluent can include any sustained release material known in the art, such as glyceryl monostearate or glyceryl distearate, alone or mixed with a wax.

As used herein, the term "pharmaceutical composition" refers to a composition containing one or more active compounds described herein, or a pharmaceutically acceptable isomer, racemate, hydrate, solvate, isotope or salt thereof, formulated with a pharmaceutically acceptable carrier, which can also include other additives, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein. Conventional procedures and ingredients for the selection and preparation of suitable formulations are described, for example, in *Remington: The Science and Practice of Pharmacy,* $21^{st}$ Ed., Gennaro, Ed., Lippencott Williams & Wilkins (2005) and in The United States Pharmacopeia: The National Formulary (USP 36 NF31), published in 2013.

As used herein, the term "pharmaceutically acceptable carrier" refers to any ingredient other than the disclosed compounds, or a pharmaceutically acceptable isomer, racemate, hydrate, solvate, isotope or salt thereof (e.g., a carrier capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The formulations can be mixed with auxiliary agents which do not deleteriously react with the active compounds. Such additives can include wetting agents, emulsifying and suspending agents, salt for influencing osmotic pressure, buffers and/or coloring substances, preserving agents, sweetening agents, or flavoring agents. The compositions can also be sterilized if desired.

The route of administration can be any route which effectively transports the active compound of the invention to the appropriate or desired site of action, such as oral, nasal, pulmonary, buccal, subdermal, intradermal, transdermal, or parenteral, e.g., rectal, depot, subcutaneous, intravenous, intraurethral, intramuscular, intranasal, ophthalmic solution, or an ointment, the oral route being preferred.

Dosage forms can be administered once a day, or more than once a day, such as twice or thrice daily. Alternatively, dosage forms can be administered less frequently than daily, such as every other day, or weekly, if found to be advisable by a prescribing physician. Dosing regimens include, for example, dose titration to the extent necessary or useful for the indication to be treated, thus allowing the patient's body to adapt to the treatment and/or to minimize or avoid unwanted side effects associated with the treatment. Other dosage forms include delayed or controlled-release forms. Suitable dosage regimens and/or forms include those set out, for example, in the latest edition of the Physicians' Desk Reference, incorporated herein by reference.

In another embodiment, there are provided methods of making a composition comprising a compound of any one of Formulas (I)-(VI), including formulating the same with a pharmaceutically acceptable carrier or diluent. In some embodiments, the pharmaceutically acceptable carrier or diluent is suitable for oral administration. In some such embodiments, the methods can further include the step of formulating the composition into a tablet or capsule. In other embodiments, the pharmaceutically acceptable carrier or diluent is suitable for parenteral administration. In some such embodiments, the methods further include the step of lyophilizing the composition to form a lyophilized preparation.

In another embodiment, a method of treating a subject having a neurodegenerative disease is provided, the method comprising administering to the subject a pharmaceutically effective amount of a compound having the structure of any one of Formulas (I)-(VI) or pharmaceutically acceptable isomer, racemate, hydrate, solvate, or salt thereof, or a pharmaceutical composition thereof. In one embodiment, the neurodegenerative disease is a demyelinating disease. In another embodiment, the neurodegenerative disease is X-linked adrenoleukodystrophy or multiple sclerosis. In one embodiment, the neurodegenerative disease is acute disseminated encephalomyelitis, acute hemorrhagic leukoencephalitis, adult Refsum disease, Alexander disease, Alzheimer's disease, Balo concentric sclerosis, Canavan disease, central pontine myelinolysis, cerebral palsy, cerebrotendineous xanthomatosis, chronic inflammatory demyelinating polyneuropathy, Devic's syndrome, diffuse myelinoclastic sclerosis, Guillain-Barre syndrome, idiopathic inflammatory demyelinating disease, infantile Refsum disease, Krabbe disease, Leber hereditary optic neuropathy, Marburg multiple sclerosis, Marchiafava-Bignami disease, metachromatic leukodystrophy, multifocal motor neuropathy, paraproteinemic demyelinating polyneuropathy, Pelizaeus-Merzbacher disease, peroneal muscular atrophy, progressive multifocal leukoencephalopathy, transverse myelitis, tropical spastic paraparesis, van der Knaap disease, X-linked adrenoleukodystrophy, or Zellweger syndrome.

In another embodiment, a method of treating a subject having Alzheimer's disease is provided, the method comprising administering to the subject a pharmaceutically effective amount of a compound having the structure of any one of Formulas (I)-(VI) or pharmaceutically acceptable isomer, racemate, hydrate, solvate, isotope or salt thereof, or a pharmaceutical composition thereof.

In another embodiment, a method of treating a subject having acute disseminated encephalomyelitis (ADEM), acute hemorrhagic leukoencephalitis (AHL or AHLE), adult Refsum disease, infantile Refsum disease, Alexander disease, Alzheimer's disease, Balo concentric sclerosis, Canavan disease, central pontine myelinolysis (CPM), cerebral palsy, cerebrotendineous xanthomatosis, chronic inflammatory demyelinating polyneuropathy (CIDP), Devic's syndrome, diffuse myelinoclastic sclerosis, encephalomyelitis, Guillain-Barre syndrome, idiopathic inflammatory demyelinating disease (IIDD), Krabbe disease, Leber hereditary optic neuropathy, leukodystrophy, Marburg multiple sclerosis, Marchiafava-Bignami disease, metachromatic leukodystrophy (MLD), multifocal motor neuropathy (MMN), multiple sclerosis (MS), paraproteinemic demyelinating polyneuropathy, Pelizaeus-Merzbacher disease (PMD), progressive multifocal leukoencephalopathy (PML), tropical spastic paraparesis (TSP), X-linked adrenoleukodystrophy (X-ALD, ALO, or X-linked ALO), or Zellweger syndrome is provided, the method comprising administering to the subject a pharmaceutically effective amount of a compound having the structure of any one of Formulas (I)-(VI) or pharmaceutically acceptable isomer, racemate, hydrate, solvate, or salt thereof, or a pharmaceutical composition thereof.

In another embodiment, a compound having the structure of any one of Formulas (I)-(VI) or pharmaceutically acceptable isomer, racemate, hydrate, solvate, or salt thereof, or a pharmaceutical composition thereof is provided for use in the treatment of a neurodegenerative disease. In one embodiment, the neurodegenerative disease is a demyelinating disease. In another embodiment, the neurodegenerative disease is X-linked adrenoleukodystrophy or multiple sclerosis. In another embodiment, the neurodegenerative disease is acute disseminated encephalomyelitis, acute hemorrhagic leukoencephalitis, adult Refsum disease, Alexander disease, Alzheimer's disease, balo concentric sclerosis, Canavan disease, central pontine myelinolysis, cerebral palsy, cerebrotendineous xanthomatosis, chronic inflammatory demyelinating polyneuropathy, Devic's syndrome, diffuse myelinoclastic sclerosis, Guillain-Barre syndrome, idiopathic inflammatory demyelinating disease, infantile Refsum disease, Krabbe disease, Leber hereditary optic neuropathy, Marburg multiple sclerosis, Marchiafava-Bignami disease, metachromatic leukodystrophy, Multifocal motor neuropathy, paraproteinemic demyelinating polyneuropathy, Pelizaeus-Merzbacher disease, peroneal muscular atrophy, progressive multifocal leukoencephalopathy, transverse myelitis, tropical spastic paraparesis, van der Knaap disease, X-linked adrenoleukodystrophy, or Zellweger syndrome.

In another embodiment, a compound having the structure of any one of Formulas (I)-(VI) or pharmaceutically acceptable isomer, racemate, hydrate, solvate, or salt thereof, or a pharmaceutical composition thereof is provided for use in the treatment of Alzheimer's disease.

In another embodiment, a compound having the structure of any one of Formula (I)-(VI) or pharmaceutically acceptable isomer, racemate, hydrate, solvate, or salt thereof, or a pharmaceutical composition thereof is provided for use in the treatment of acute disseminated encephalomyelitis (ADEM), acute hemorrhagic leukoencephalitis (AHL or AHLE), adult Refsum disease, infantile Refsum disease, Alexander disease, Alzheimer's disease, Balo concentric sclerosis, Canavan disease, central pontine myelinolysis (CPM), cerebral palsy, cerebrotendineous xanthomatosis, chronic inflammatory demyelinating polyneuropathy (CIDP), Devic's syndrome, Diffuse myelinoclastic sclerosis, encephalomyelitis, Guillain-Barre syndrome, idiopathic inflammatory demyelinating disease (IIDD), Krabbe disease, Leber hereditary optic neuropathy, leukodystrophy, Marburg multiple sclerosis, Marchiafava-Bignami disease, metachromatic leukodystrophy (MLD), multifocal motor neuropathy (MMN), multiple sclerosis (MS), paraproteinemic demyelinating polyneuropathy, PelizaeusMerzbacher disease (PMD), progressive multifocal leukoencephalopathy (PML), tropical spastic paraparesis (TSP), X-linked adrenoleukodystrophy (X-ALD, ALO, or X-linked ALO), or Zellweger syndrome.

As used herein, the term "administration" refers to providing a compound of any one of Formulas (I)-(VI), or a pharmaceutical composition comprising the same, to a subject as described herein. The compound or composition can be administered by another person to the subject or it can be self-administered by the subject. Non-limiting examples of routes of administration are oral, parenteral (e.g., intravenous), or topical.

As used herein, the term "subject" refers to an animal (e.g., a mammal, such as a human). A subject to be treated according to the methods described herein may be one who has been diagnosed with a neurodegenerative disease involving demyelination, insufficient myelination, or underdevelopment of a myelin sheath, e.g., a subject diagnosed with multiple sclerosis or cerebral palsy, or one at risk of developing the condition. Diagnosis may be performed by any method or technique known in the art. One skilled in the art will understand that a subject to be treated according to the present disclosure may have been subjected to standard tests or may have been identified, without examination, as one at risk due to the presence of one or more risk factors associated with the disease or condition.

As used herein, the term "treatment" refers to an intervention that ameliorates a sign or symptom of a disease or pathological condition. As used herein, the terms "treatment", "treat" and "treating," with reference to a disease, pathological condition or symptom, also refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease. A prophylactic treatment is a treatment administered to a subject who does not exhibit signs of a disease or exhibits only early signs, for the purpose of decreasing the risk of developing pathology. A therapeutic treatment is a treatment administered to a subject after signs and symptoms of the disease have developed.

As used herein, the term "effective amount" refers to a quantity of a specified agent sufficient to achieve a desired effect in a subject being treated with that agent. Ideally, an effective amount of an agent is an amount sufficient to inhibit or treat the disease without causing substantial toxicity in the subject. The effective amount of an agent will be dependent on the subject being treated, the severity of the affliction, and the manner of administration of the pharmaceutical composition. Methods of determining an effective amount of the disclosed compound sufficient to achieve a desired effect in a subject will be understood by those of skill in the art in light of this disclosure.

As used herein, the terms "acute disseminated encephalomyelitis" and "ADEM" refer to an immune-mediated demyelinating disease of the central nervous system. ADEM usually occurs following a viral infection, but may also appear following vaccination or following bacterial or parasitic infection. In some cases, ADEM develops spontaneously. The disease involves autoimmune demyelination, similar to multiple sclerosis, and is therefore considered a multiple sclerosis borderline disease. ADEM produces multiple inflammatory lesions in the brain and spinal cord, particularly in the white matter. The lesions are typically found in the subcortical and central white matter and cortical gray-white junction of both cerebral hemispheres, cerebellum, brainstem, and spinal cord, but periventricular white matter and gray matter of the cortex, thalami and basal ganglia may also be involved. When a patient suffers more than one demyelinating episode, the disease is referred to as recurrent disseminated encephalomyelitis or multiphasic disseminated encephalomyelitis.

As used herein, the terms "acute hemorrhagic leukoencephalitis," "AHL," and "AHLE" refer to a hyperacute and frequently fatal form of ADEM. This disease is also known as acute necrotizing encephalopathy (ANE), acute hemorrhagic encephalomyelitis (AHEM), acute necrotizing hemorrhagic leukoencephalitis (ANHLE), Weston-Hurst syndrome, or Hurst's disease.

As used herein, the term "adult Refsum disease" refers to an autosomal recessive neurological disease that is associated with the over-accumulation of phytanic acid in cells and tissues. Adult Refsum disease is divided into the adult Refsum disease 1 and adult Refsum disease 2 subtypes. Individuals with Refsum disease present with neurologic damage, cerebellar degeneration, and peripheral neuropathy. Onset is most commonly in childhood/adolescence with a progressive course, although periods of stagnation or remission occur. Symptoms also include ataxia, scaly skin (ichthyosis), difficulty hearing, and eye problems including cataracts and night blindness.

As used herein, the term "Alexander disease" refers to a very rare, congenital demyelinating disease. The disease primarily affects infants and children, causing developmental delay and changes in physical characteristics. Alexander disease is a type of leukodystrophy.

As used herein, the term "Alzheimer's disease" refers to the most common form of dementia. Symptoms of Alzheimer's disease include memory loss, confusion, irritability, aggression, mood swings and trouble with language. This disease is characterized by the loss of neurons and synapses in the cerebral cortex and certain subcortical regions. The loss results in gross atrophy of the affected regions, including degeneration in the temporal lobe, and parts of the frontal cortex and cingulate gyrus. Amyloid plaques and neurofibrillary tangles are visible by microscopy in brains of those afflicted with this disease. The cause of Alzheimer's disease is unknown; however, several hypotheses exist, including that the disease is caused by age-related myelin breakdown in the brain.

As used herein, the term "Balo concentric sclerosis" refers to a demyelinating disease similar to standard multiple sclerosis, but with the particularity that the demyelinated tissues form concentric layers. Patients with this disease can survive and/or have spontaneous remission. Typically, the clinical course is primary progressive, but a relapsing-remitting course has been reported.

As used herein, the term "Canavan disease" refers to an autosomal recessive degenerative disorder that causes progressive damage to nerve cells in the brain. Canavan disease is a leukodystrophy and is one of the most common degenerative cerebral diseases of infancy. This disease is also called Canavan-Van Bogaert-Bertrand disease, aspartoacylase deficiency and aminoacylase 2 deficiency.

As used herein, the terms "Central pontine myelinolysis" and "CPM" refer to a neurologic disease caused by severe damage of the myelin sheath of nerve cells in the brainstem, more precisely in the area termed the pons. The most common cause is the rapid correction of low blood sodium levels (hyponatremia). Frequently observed symptoms in this disorder are sudden para or quadraparesis, dysphagia, dysarthria, diplopia and loss of consciousness. The patient may experience locked-in syndrome where cognitive function is intact, but all muscles are paralyzed with the exception of eye blinking.

As used herein, the term "cerebral palsy" refers to a group of permanent, non-progressive movement disorders that cause physical disability. Cerebral palsy is caused by damage to the motor control centers of the developing brain and can occur during pregnancy, during childbirth, or after birth up to about age three. Patients with cerebral palsy exhibit damage to myelin sheaths.

As used herein, the term "cerebrotendineous xanthomatosis" refers to an inherited disorder associated with the deposition of a form of cholesterol (cholestanol) in the brain and other tissues and with elevated levels of cholesterol in plasma but with normal total cholesterol level. It is characterized by progressive cerebellar ataxia beginning after puberty and by juvenile cataracts, juvenile or infantile onset chronic diarrhea, childhood neurological deficit, and tendineous or tuberous xanthomas. This disorder is an autosomal recessive form of xanthomatosis. It falls within a group of genetic disorders called the leukodystrophies.

As used herein, the terms "chronic inflammatory demyelinating polyneuropathy" and "CIDP" refer to an acquired immune-mediated inflammatory disorder of the peripheral nervous system. The disorder is sometimes called chronic relapsing polyneuropathy (CRP) or chronic inflammatory demyelinating polyradiculoneuropathy (because it involves the nerve roots). CIDP is closely related to Guillain-Barre syndrome and it is considered the chronic counterpart of that acute disease. Its symptoms are also similar to progressive inflammatory neuropathy. An asymmetrical variant of CIDP is known as Lewis-Sumner syndrome. The pathologic hallmark of the disease is loss of the myelin sheath.

As used herein, the term "demyelinating disease" refers to any disease of the nervous system in which myelin is damaged or lost, or in which the growth or development of the myelin sheath is impaired. Demyelination inhibits the conduction of signals in the affected nerves, causing impairment in sensation, movement, cognition, or other functions for which nerves are involved. Demyelinating diseases have a number of different causes and can be hereditary or acquired. In some cases, a demyelinating disease is caused by an infectious agent, an autoimmune response, a toxic agent or traumatic injury. In other cases, the cause of the demyelinating disease is unknown ("idiopathic") or develops from a combination of factors.

As used herein, the term "Devic's syndrome" refers to an autoimmune, inflammatory disorder in which a person's immune system attacks the optic nerves and spinal cord, which results in inflammation of the optic nerve (optic neuritis) and the spinal cord (myelitis). Spinal cord lesions lead to varying degrees of weakness or paralysis in the legs or arms, loss of sensation, and/or bladder and bowel dysfunction. Although inflammation may also affect the brain, the lesions are different from those observed in MS. Devic's syndrome is similar to MS in that the body's immune system attacks the myelin surrounding nerve cells. Unlike standard MS, the attacks are not believed to be mediated by the immune system's T cells but rather by antibodies called NMO-IgG. These antibodies target a protein called aquaporin 4 in the cell membranes of astrocytes which acts as a channel for the transport of water across the cell membrane. Devic's syndrome is also known as Devic's syndrome or neuromyelitis optica (NMO).

As used herein, the term "diffuse myelinoclastic sclerosis" refers to an uncommon neurodegenerative disease that presents clinically as pseudotumoral demyelinating lesions. It usually begins in childhood, affecting children between 5 and 14 years old; however, cases in adults are possible. This disease is considered one of the borderline forms of MS and is sometimes referred to as Schilder's disease.

As used herein, the term "encephalomyelitis" refers to inflammation of the brain and spinal cord.

As used herein, the term "Guillain-Barré syndrome" refers to an acute polyneuropathy, a disorder affecting the peripheral nervous system. Ascending paralysis, weakness beginning in the feet and hands and migrating towards the trunk, is the most typical symptom, and some subtypes cause change in sensation or pain, as well as dysfunction of the autonomic nervous system. It can cause life-threatening complications, in particular if the respiratory muscles are affected or if the autonomic nervous system is involved. This disease is usually triggered by an infection. Acute inflammatory demyelinating polyneuropathy (AIDP) is the most common subtype of this disease. Other subtypes of Guillain-Barré syndrome include Miller Fischer syndrome, acute motor axonal neuropathy (Chinese paralytic syndrome), acute motor sensory axonal neuropathy, acute panautonomic neuropathy, and Bickerstaff's brainstem encephalitis.

As used herein, the terms "idiopathic inflammatory demyelinating disease" and "IIDD" refer to a broad spectrum of central nervous system disorders that can usually be differentiated on the basis of clinical, imaging, laboratory and pathological findings. Idiopathic inflammatory demyelinating diseases are sometimes known as borderline forms of multiple sclerosis. IIDD generally refers to a collection of multiple sclerosis variant diseases, including but not limited to, optic-spinal MS, Devic's disease, ADEM, acute hemorrhagic leukoencephalitis, Balo concentric sclerosis, Schilder disease, Marburg multiple sclerosis, tumefactive multiple sclerosis and solitary sclerosis.

As used herein, the term "infantile Refsum disease" refers to a peroxisome biogenesis disorder associated with deficiencies in the catabolism of very long chain fatty acids and branched chain fatty acids (such as phytanic acid) and plasmalogen biosynthesis. Infantile Refsum disease is a rare, autosomal recessive congenital disorder, and one of three peroxisome biogenesis disorders that belong to the Zellweger spectrum of peroxisome biogenesis disorders.

As used herein, the term "Krabbe disease" refers to a rare, often fatal degenerative disorder that affects the myelin sheath of the nervous system. It is a form of sphingolipidosis, as it involves dysfunctional metabolism of sphingolipids. This condition is inherited in an autosomal recessive pattern. Krabbe disease is also known as globoid cell leukodystrophy or galactosylceramide lipidosis.

As used herein, the term "Leber hereditary optic neuropathy" refers to a mitochondrially inherited (transmitted from mother to offspring) degeneration of retinal ganglion cells (RGCs) and their axons that leads to an acute or subacute loss of central vision; this affects predominantly young adult males.

As used herein, the term "leukodystrophy" refers to a group of diseases that affects the growth or development of the myelin sheath.

As used herein, the term "leukoencephalopathy" refers to any of a group of diseases affecting the white substance of the brain; can refer specifically to several diseases including, for example, "leukoencephalopathy with vanishing white matter" and "toxic leukoencephalopathy." Leukoencephalopathies are leukodystrophy-like diseases.

As used herein, the term "Marburg multiple sclerosis" refers to a condition in which the central nervous system has multiple demyelinating lesions with atypical characteristics for those of standard multiple sclerosis. This disease is a borderline form of multiple sclerosis and is also known as tumefactive multiple sclerosis or fulminant multiple sclerosis. It is called tumefactive because the lesions are "tumor-like" and they mimic tumors clinically, radiologically and sometimes pathologically.

As used herein, the term "Marchiafava-Bignami disease" refers to a progressive neurological disease characterized by corpus callosum demyelination and necrosis and subsequent atrophy. It is classically associated with chronic alcoholics.

As used herein, the terms "metachromatic leukodystrophy" and "MLD" refer to a lysosomal storage disease that is commonly listed in the family of leukodystrophies, as well as in the sphingolipidoses as it affects the metabolism of sphingolipids. MLD is directly caused by a deficiency of the enzyme arylsulfatase A.

As used herein, the terms "multifocal motor neuropathy" and "MMN" refer to a progressively worsening condition where muscles in the extremities gradually weaken. This disorder, a motor neuropathy syndrome, is sometimes mistaken for amyotrophic lateral sclerosis (ALS) because of the similarity in the clinical picture, especially if muscle fasciculations are present. MMN is usually asymmetric and is thought to be autoimmune.

As used herein, the terms "multiple sclerosis" and "MS" refer to a slowly progressive CNS disease characterized by disseminated patches of demyelination in the brain and spinal cord, resulting in multiple and varied neurological symptoms and signs, usually with remissions and exacerbation. The cause of MS is unknown but an immunological abnormality is suspected. An increased family incidence suggests genetic susceptibility, and women are somewhat more often affected than men. The symptoms of MS include weakness, lack of coordination, paresthesias, speech disturbances, and visual disturbances, most commonly double vision. More specific signs and symptoms depend on the location of the lesions and the severity and destructiveness of the inflammatory and sclerotic processes. Relapsing-remitting multiple sclerosis (RRMS) is a clinical course of MS that is characterized by clearly defined, acute attacks with full or partial recovery and no disease progression between attacks. Secondary-progressive multiple sclerosis (SPMS) is a clinical course of MS that initially is relapsing-remitting, and then becomes progressive at a variable rate, possibly with an occasional relapse and minor remission. Primary-progressive multiple sclerosis (PPMS) presents initially in the progressive form. A clinically isolated syndrome is the first neurologic episode, which is caused by inflammation/demyelination at one or more sites in the CNS. Progressive-relapsing multiple sclerosis (PRMS) is a rare form of MS (~5%) characterized by a steadily worsening disease state from onset, with acute relapses but no remissions.

As used herein, the term "myelin" refers to a lipid substance forming a sheath (known as the myelin sheath) around the axons of certain nerve fibers. Myelin is an electrical insulator that serves to speed the conduction of nerve impulses in nerve fibers. "Myelination" (also "myelinization") refers to the development or formation of a myelin sheath around a nerve fiber. Similarly, "remyelination" (also, "remyelinization") refers to the repair or reformation of the myelin sheath, such as following injury, exposure to a toxic agent, or an inflammatory response, or during the course of a demyelinating disease.

As used herein, the term "neurodegenerative disease" refers to any type of disease that is characterized by the progressive deterioration of the nervous system.

As used herein, the term "neuropathy" refers to a functional disturbance or pathological change in the peripheral nervous system. Axonal neuropathy refers to a disorder disrupting the normal functioning of the axons.

As used herein, the term "paraproteinemic demyelinating polyneuropathy" refers to a type of peripheral neuropathy characterized by auto antibodies directed against myelin associated glycoproteins (MAG). Anti-MAG antibodies inhibit the production of myelin, thereby leading to neuropathy.

As used herein, the terms "Pelizaeus-Merzbacher disease" and "PMD" refer to a rare central nervous system disorder in which coordination, motor abilities, and intellectual function are delayed to variable extents. The disease is one in a group of genetic disorders collectively known as leukodystrophies.

As used herein, the terms "peroneal muscular atrophy" and "PMA" refer to a genetically and clinically heterogeneous group of inherited disorders of the peripheral nervous system characterized by progressive loss of muscle tissue and touch sensation across various parts of the body. This disease is also known as Charcot-Marie-Tooth disease (CMT), Charcot-Marie-Tooth neuropathy and hereditary motor and sensory neuropathy (HMSN).

As used herein, the terms "progressive multifocal leukoencephalopathy" and "PML" refer to rare and usually fatal viral disease that is characterized by progressive damage or inflammation of the white matter of the brain in multiple locations. PML occurs almost exclusively in people with severe immune deficiency. The cause of PML is a type of polyomavirus called the JC virus. The virus is widespread, with 86% of the general population presenting antibodies, but it usually remains latent, causing disease only when the immune system has been severely weakened. PML is a demyelinating disease, in which the myelin sheath covering the axons of nerve cells is gradually destroyed, impairing the transmission of nerve impulses. The disease may occur in subjects (e.g., humans) with severe immune deficiency, such as transplant patients on immunosuppressive medications or those receiving certain kinds of medications. For example, PML has been associated with administration of rituximab (off-label use in the treatment of multiple sclerosis). It affects the white matter, which is mostly composed of axons from the outermost parts of the brain (cortex). Symptoms include weakness or paralysis, vision loss, impaired speech, and cognitive deterioration.

As used herein, the term "transverse myelitis" refers to a neurological disorder caused by an inflammatory process of the grey and white matter of the spinal cord, leading to axonal demyelination. Demyelination arises idiopathically following infections or vaccination, or due to multiple sclerosis. Symptoms include weakness and numbness of the limbs as well as motor, sensory, and sphincter deficits. Severe back pain may occur in some patients at the onset of the disease.

As used herein, the terms "tropical spastic paraparesis" and "TSP" refer to an infection of the spinal cord by human T-lymphotropic virus resulting in paraparesis, weakness of the legs. TSP is also known as HTLV associated myelopathy or chronic progressive myelopathy. As the name suggests, this disease is most common in tropical regions, including the Caribbean and Africa.

As used herein, the term "Van der Knaap disease" refers to a form of hereditary CNS demyelinating disease. This disease is a type of leukodystrophy and is also known as megalencephalic leukoencephalopathy with subcortical cysts (MLC).

As used herein, the terms "X-linked adrenoleukodystrophy," "X-ALD," "ALD," and "X-linked ALD" refer to a rare, inherited metabolic disorder that leads to progressive brain damage, mental deterioration, failure of the adrenal glands, muscle spasms, blindness and eventually death. ALD is one disease in a group of inherited disorders called leukodystrophies. Adrenoleukodystrophy progressively damages myelin. X-linked ALD male patients may be divided into 7 phenotypes: childhood cerebral (progressive neurodegenerative decline leading to a vegetative state), adolescent (similar to childhood cerebral form but with a slower progression), adrenomyeloneuropathy (progressive neuropathy, paraparesis, may progress to cerebral involvement), adult cerebral (dementia, similar progression to childhood cerebral form), olivo-ponto-cerebellar (cerebral and brain stem involvement), Addison disease (adrenal insufficiency), asymptomatic (no clinical presentation, subclinical adrenal insufficiency, or AMN phenotype). X-linked ALD female patients may be divided into 5 phenotypes: asymptomatic (no neurologic or adrenal involvement), mild myelopathy, moderate to severe myelopathy (similar to male AMN phenotype), cerebral (progressive dementia and decline), and adrenal (primary adrenal insufficiency). X-linked ALD patients may progress from one phenotype to another over the course of their life. ALD is also known as Addison-Schilder disease or Siemerling-Creutzfeldt disease.

As used herein, the term "Zellweger syndrome" refers to a rare congenital disorder, characterized by the reduction or absence of functional peroxisomes in the cells of an individual. This disease is classified as a leukodystrophy and is one of three peroxisome biogenesis disorders that belong to the Zellweger spectrum of peroxisome biogenesis disorders.

Synthesis of the isotopic compounds of Formulas (I)-(VI) can be synthesized using standard synthetic techniques known to those of skill in the art, and by employing starting materials and/or intermediates with isotope substitution at the desired atom(s). For example, compounds of the present invention can be synthesized using appropriately modified synthetic procedures set forth in Schemes 1 and 2, as well as by the procedures disclosed in WO2014/178892, WO2014/178931, WO2016/134292, WO2017/201320, WO2018/032012, and WO2019/160980 (each of which are incorporated herein by reference in their entirety).

To this end, the reactions, processes, and synthetic methods described herein are not limited to the specific conditions described in the following experimental section, but rather are intended as a guide to one with suitable skill in this field. For example, reactions may be carried out in any suitable solvent, or other reagents to perform the transformation[s] necessary. Generally, suitable solvents are protic or aprotic solvents which are substantially non-reactive with the reactants, the intermediates or products at the temperatures at which the reactions are carried out (i.e., temperatures which may range from the freezing to boiling temperatures). A given reaction may be carried out in one solvent or a mixture of more than one solvent. Depending on the particular reaction, suitable solvents for a particular work-up following the reaction may be employed. Representative synthetic routes include, but are not limited, to Schemes 1-3 below.

Scheme 1

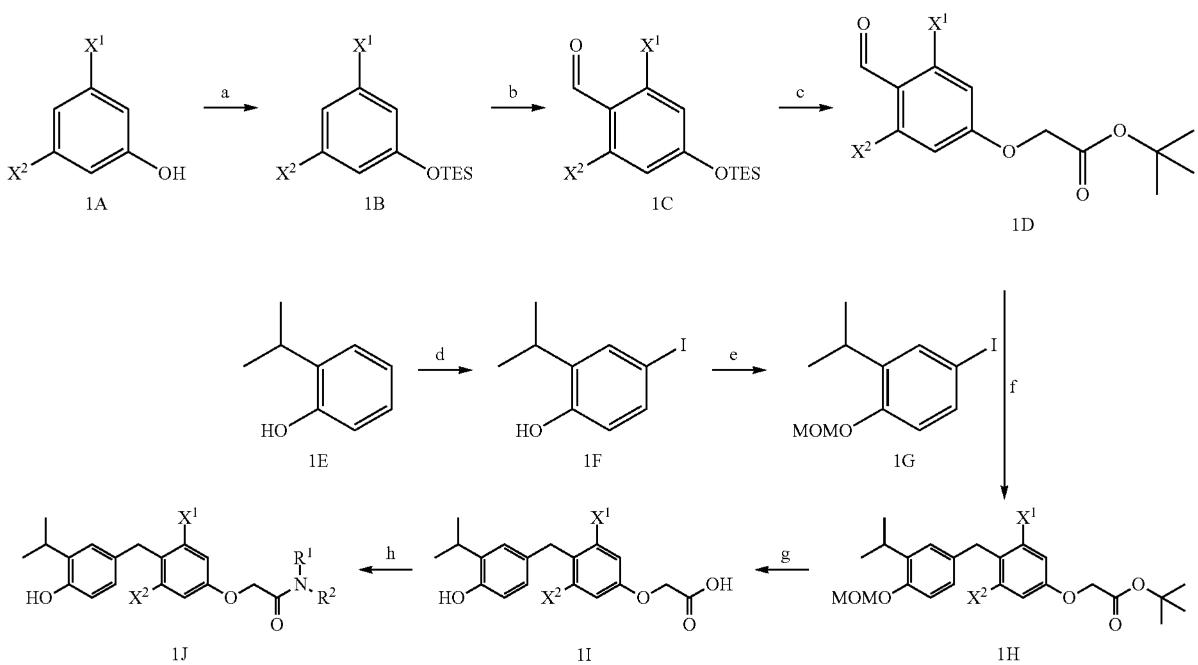

1A 1B 1C 1D 1E 1F 1G 1H 1I 1J

Reagents/Conditions: (a) triethylsilyl chloride, imidazole, DCM, 0° C.; (b) (i) nBuLi, DIA/TMP, THF, −78° C. (ii) DMF; (c) tertchloroacetate, NaI, $Cs_2CO_3$, acetone, 60-65° C.; (d) NaI, NaOH, NaOCl, MeOH, $H_2O$; (e) MOMCl, TBAI, NaOH, DCM, $H_2O$; (f) (i) iPMgCl, THF, 0° C. to RT (ii) 4, −78° C.; (g) TFA, triethylsilane, DCM, 0° C. to RT; and (h) MeOH, $H_2SO_4$, $NHR^1R^2$, 65° C. to RT.

4-Hydroxy-2,6-dihalobenzaldehyde intermediates are produced by selective deprotonation of the 4-position of trimethylsilyl ether protected 3,5-dihalophenols with lithium amide reagents. These intermediates were used in a slightly altered version of the sobetirome synthesis reported in Placzek A T and Scanlan T S, Tetrahedron 71, 5946-5951 (2015); which is incorporated by reference herein. The 4-hydroxy-2,6-dihalobenzaldehyde intermediates could not be alkylated with tertbutyl chloroacetate using the standard cesium carbonate/DMF conditions due to the halogen substitutions reducing the nucleophilicity of the phenol. However, the reaction went to completion and in good yield after converting the alkyl chloride into an alkyl iodide via an in situ Finklestein reaction.

After forming the tert-butyl oxyacetate intermediate, the carbon-carbon bond formation proceeded in the same fashion as with sobetirome by forming an arylmagnesium with 1G that attacked the benzaldehyde to form a carbinol intermediate. The arylmagnesium nucleophile will not likely exchange with aryl chlorides or bromides at cryogenic temperatures and is compatible with the tert-butyl ester protecting group. Reduction of the carbinol and deprotection of the tert-butyl ester and methoxymethyl ether protecting groups proceeded simultaneously with TFA and triethylsilane in dichloromethane.

Synthesis of isotopic sobetirome may be achieved in the manner illustrated above in Scheme 1; namely, stopping with intermediate 1L, where wherein both $X^1$ and $X^2$ are methyl, and employing starting materials and/or intermediates with isotope substitution at the desired atom(s).

Scheme 2

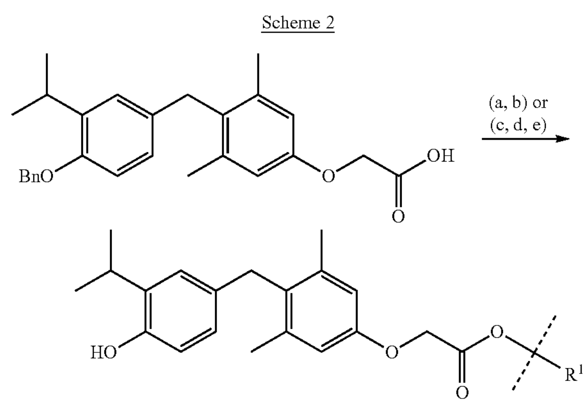

Reagents/Conditions: (a) (i) oxalyl chloride, DCM, DMF, (ii) alcohol or N-Cbz-amino alcohol, DMAP or TEA/DMAP, DCM or THF; (b) 10% Pd/C, $Et_3SiH$, MeOH; (c) (i) oxalyl chloride, DCM, DMF (ii) N-Boc-amino alcohol, DMAP, DCM or THF; (d) 10% Pd/C, $Et_3SiH$, MeOH, THF; and (e) 1 M HCl (ethyl acetate).

Similarly, isotopic ester derivatives of sobetirome, may be prepared in a similar fashion as depicted in Scheme 2 above, starting with intermediate 1L in Scheme 1 (with a benzyl-protected alcohol), wherein both $X^1$ and $X^2$ are methyl and using Cbz-protected amino alcohols, and again employing starting materials and/or intermediates with isotope substitution at the desired atom(s). The use of the cbz-protecting group allows a single deprotection (10% Pd/C, $Et_3SiH$) to remove both the benzyl and cbz protecting groups.

Scheme 3

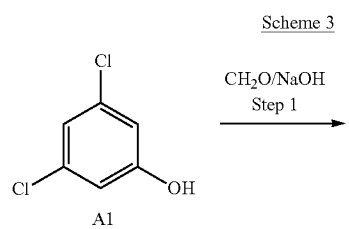

A1

-continued

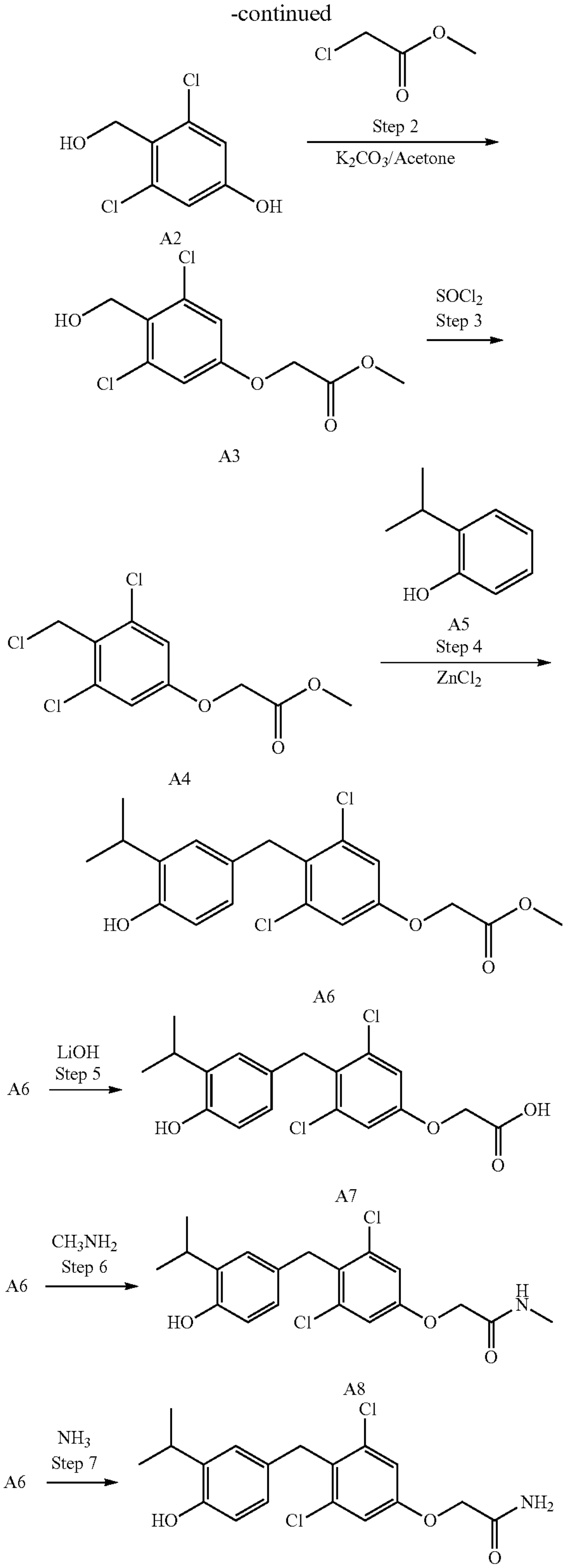

A2

A3

A4

A6

A7

A8

A9

Compounds of the present invention can also be prepared according to Scheme 3 above. Referring to Scheme 3, substituted phenol (A1) is reacted with a formaldehyde equivalent (for example, aqueous formaldehyde or paraformaldehyde or dimethoxymethane or the like) to give a hydroxymethyl derivative (A2), which is subsequently reacted with an activated acetate moiety (for example ethyl chloroacetate or methyl bromoacetate or the like) in the presence of base, selectively at the phenolic oxygen, to provide intermediate (A3). The hydroxymethyl group is activated (for example, through reaction with thionyl chloride or oxalyl chloride or p-toluenesulfonylchloride or the like) to give a chloromethyl derivative (A4) (or the corresponding tosylate, or mesylate, or bromomethyl analog, or the like), which is condensed with a 2-substituted phenol (A5) in the presence of a Lewis acid (like zinc chloride, or aluminum chloride, or the like) to give an ester (A6). Alternatively, intermediate alcohol (A3) can be reacted directly with phenol (A5) in the presence of a protic acid (for example using sulfuric acid or the like), or a Lewis acid (for example boron trifluoride etherate or the like) to provide an ester (A6). Hydrolysis of the ester group of intermediate A6, for example using aqueous sodium hydroxide (if $R^1$ is methyl) or TFA (if $R^1$ is t-butyl)) provides acid (A7) of the present invention. If desired, acid (A7) can be converted to amides (A8 or A9) by condensing with the corresponding amine (for example methylamine or propylamine or 2-sulfonylethylamine or the like) in the presence of a coupling agent (for example DDC or EDCI or the like), or by forming an activated intermediate (for example the corresponding acid chloride busing thionyl chloride or the like). Alternatively, if desired, either esters (A6), or acids (A7) may be heated with an amine $R^{2a}R^{2b}NH$, for example methylamine or propylamine or 2-sulfonylethylamine or the like, to give amides (A8 or A9) of the present invention.

EXAMPLES

The invention is further illustrated by the following examples. The examples below are non-limiting are merely representative of various aspects of the invention. Solid and dotted wedges within the structures herein disclosed illustrate relative stereochemistry, with absolute stereochemistry depicted only when specifically stated or delineated.

$^1$H NMR are taken on a Bruker 400. All $^1$H NMR are calibrated to the NMR solvent reference peak (D6-acetone, CDCl3). Anhydrous tetrahydrofuran (THF) and dimethylformamide (DMF) are obtained from a Seca Solvent System. All other solvents used are purchased from Sigma-Aldrich or Fisher. Purity analysis of final compounds was determined to be >95% by HPLC. HPLC analysis was performed on a Varian ProStar HPLC with an Agilent Eclipse Plus C18 5 μM column (4.6×250 mm) with a gradient of 10% to 95% acetonitrile (0.1% TFA) over 15 minutes.

As used above, and throughout the description of the invention, the following abbreviations, unless otherwise indicated, shall be understood to have the following meanings:

| | |
|---|---|
| ACN or MeCN | acetonitrile |
| AcOH | acetic acid |
| Ac | acetyl |
| Bn | benzyl |
| BOC or Boc | tert-butyl carbamate |
| t-Bu | tert-butyl |
| Cy | cyclohexyl |
| DBA or dba | dibenzylideneacetone |
| CDI | 1,1-carbonyldiimidazole |
| DCE | dichloroethane ($ClCH_2CH_2Cl$) |
| DCM | dichloromethane ($CH_2Cl_2$) |

-continued

| | |
|---|---|
| DIPEA or DIEA | diisopropylethylamine |
| DMAP | 4-(N,N-dimethylamino)pyridine |
| DME | 1,2-dimethoxyethane |
| DMF | N,N-dimethylformamide |
| DMA | N,N-dimethylacetamide |
| DMSO | dimethylsulfoxide |
| EDC or EDCI | N-(3-dimethylaminopropyl)-N'-ethylcarbodiimide hydrochloride |
| eq | equivalent(s) |
| Et | ethyl |
| $Et_2O$ | diethyl ether |
| EtOH | ethanol |
| EtOAc | ethyl acetate |
| HOBt | 1-hydroxybenzotriazole |
| HPLC | high performance liquid chromatography |
| KHMDS | potassium bis(trimethylsilyl)amide |
| NaHMDS | sodium bis(trimethylsilyl)amide |
| LiHMDS | lithium bis(trimethylsilyl)amide |
| LAH | lithium aluminum anhydride |
| LCMS | liquid chromatography mass spectrometry |
| Me | methyl |
| MeOH | methanol |
| MS | mass spectroscopy |
| Ms | mesyl |
| MTBE | methyl tert-butyl ether |
| NBS | N-bromosuccinimide |
| NMM | N-methyl-morpholine |
| NMP | N-methyl-pyrrolidin-2-one |
| NMR | nuclear magnetic resonance |
| Ph | phenyl |
| PPTS | pyridium p-toluenesulfonate |
| iPr/i-Pr | iso-propyl |
| rt | room temperature |
| TFA | trifluoroacetic acid |
| TEA | triethylamine |
| THE | tetrahydrofuran |
| TLC | thin layer chromatography |

Following Scheme 3 above, the following compounds were prepared.

Example A

Step 1

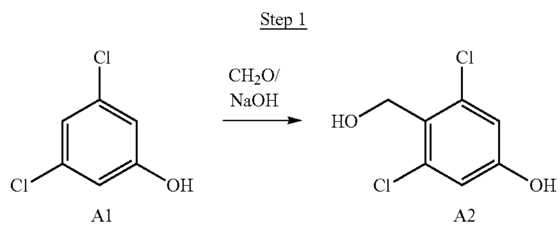

A1 A2

To a solution of NaOH (6.7 g, 169 mmol) in water (20 mL) was added A1 3,5-dichlorophenol (25.0 g, 153 mmol). The mixture was heated to 45° C. and 36% aqueous formaldehyde (12.4 g, 153 mmol) was added dropwise slowly. The mixture was stirred at 45° C. for 2 h, then cooled to rt. The pH was adjusted to ~3-4 with 1N HCl, and the mixture was stirred at rt for 20 min. The solid was collected by filtration, washed with water (50 mL) and dried to afford the product A2 3,5-dichloro-4-(hydroxymethyl) phenol (11.5 g, 59.6 mmol, 39% yield) as an off-white solid. TLC: EtOAc/pet. ether=1/3; Rf=0.36. $^1$H NMR (400 MHZ, DMSO-$d_6$) δ 10.02 (s, 1H), 6.82 (s, 2H), 4.98 (s, 1H), 4.57 (d, J=2.1 Hz, 2H).

Step 2

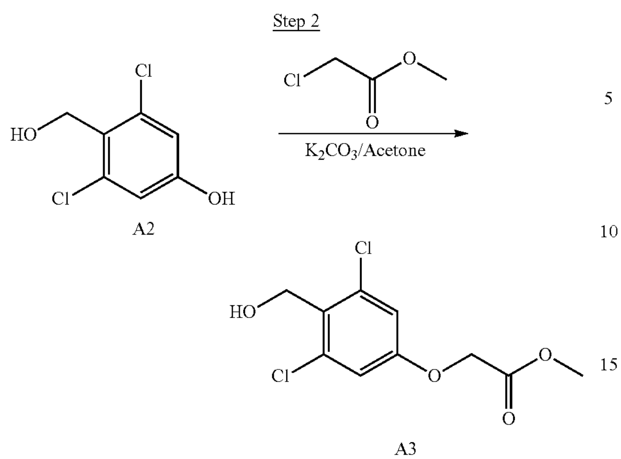

A2

A3

To a solution of A2 3,5-dichloro-4-(hydroxymethyl) phenol (3.0 g, 15.5 mmol) in acetone (40 mL) were added potassium carbonate (3.22 g, 23.3 mmol) and methyl 2-chloroacetate (2.02 g, 18.6 mmol). The mixture was heated to reflux for 2 h. The mixture was cooled to rt, diluted with water (120 mL), and extracted with EtOAc (80 mL*3). The combined organic phase was washed with brine (200 mL), dried over $Na_2SO_4$, and concentrated in vacuo. The residue was purified by silica gel column chromatography (Pet. ether/EtOAc=20/1 to 5/1) to afford A3 methyl 2-[3,5-dichloro-4-(hydroxymethyl)phenoxy]acetate (2.0 g, 7.54 mmol, 48.5% yield) as a white solid. TLC: EtOAc/pet. ether=1/5; Rf=0.28. $^1H$ NMR (400 MHz, DMSO-$d_6$) δ 7.10 (s, 2H), 5.08 (t, J=5.3 Hz, 1H), 4.91 (s, 2H), 4.61 (d, J=5.3 Hz, 2H), 3.70 (s, 3H).

Step 3

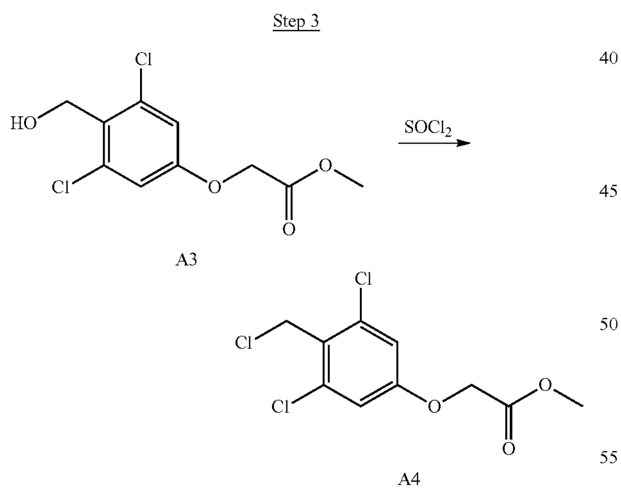

A3

A4

To a mixture of A3 methyl 2-[3,5-dichloro-4-(hydroxymethyl)-phenoxy]acetate (1.0 g, 3.77 mmol) in DCM (10 mL) was added $SOCl_2$ (0.67 g, 5.66 mmol). The mixture was stirred at rt for 1 hr and concentrated in vacuo to afford crude A4 methyl 2-[3,5-dichloro-4-(chloromethyl)phenoxy]acetate (1.0 g, 3.53 mmol, 93.5% yield) as light yellow solid which was used without further purification. TLC: EtOAc/pet. ether=1/5; Rf=0.72. $^1H$ NMR (400 MHz, DMSO-$d_6$) δ 7.21 (s, 2H), 4.94 (s, 2H), 4.85 (s, 2H), 3.71 (s, 3H).

Step 4

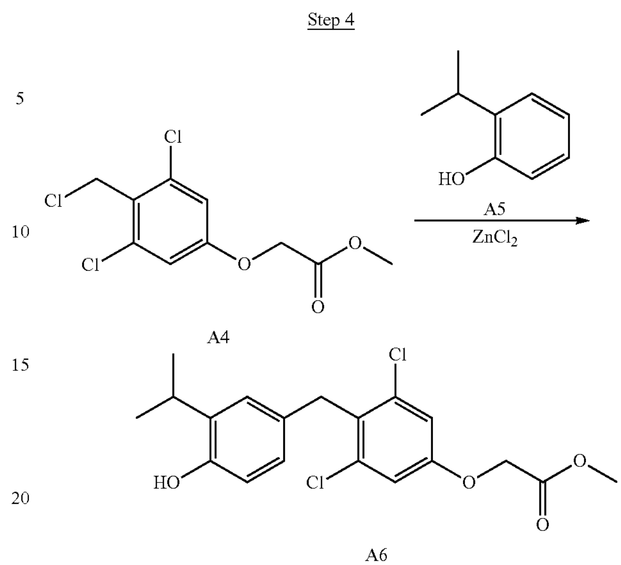

A4

A6

To a solution of A4 methyl 2-[3,5-dichloro-4-(chloromethyl)phenoxy]acetate (500 mg, 1.76 mmol) in 1,2-dichloroethane (10 mL) were added A5 2-isopropylphenol (720.50 mg, 5.29 mmol) and $ZnCl_2$ (4.4 mL, 4.41 mmol, 1M in THF). The solution was heated overnight at 85° C. The solution was cooled to rt, washed with brine (10 mL), dried over $Na_2SO_4$, and concentrated in vacuo; the residue was purified by silica gel column chromatography (pet. ether/EtOAc=30/1 to 10/1 to 5/1) to afford A6 methyl 2-[3,5-dichloro-4-[(4-hydroxy-3-isopropyl-phenyl)methyl]phenoxy]acetate (350 mg, 913 μmol, 51.8% yield) as a light yellow solid. TLC: EtOAc/pet. ether=1/5; Rf=0.45. $^1H$ NMR (400 MHz, DMSO-$d_6$) δ 9.08 (s, 1H), 7.15 (s, 2H), 6.98 (d, J=1.9 Hz, 1H), 6.71-6.62 (m, 2H), 4.90 (s, 2H), 4.04 (d, J=1.5 Hz, 2H), 3.70 (s, 3H), 3.19-3.08 (m, 1H), 1.11 (d, J=6.9 Hz, 6H).

Step 5

A6

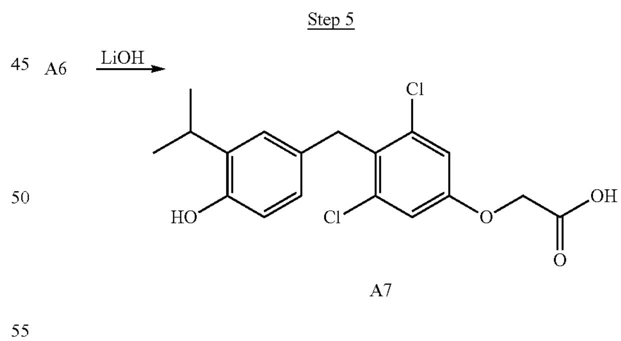

A7

To a solution of A6 methyl 2-[3,5-dichloro-4-[(4-hydroxy-3-isopropyl-phenyl)methyl]phenoxy]acetate (28.0 g, 73.1 mmol, 1.0 eq) in THF (250 mL) was added a solution of LiOH—$H_2O$ (9.0 g, 219 mmol, 3.0 eq) in water (500 mL). The mixture was stirred 1 hr, then partially concentrated to remove the THF. The aqueous phase was then extracted with MTBE (100 mL×3), after which the aqueous phase was adjusted to pH~2-3 with HCl (1N). The resulting precipitate was collected and dried in a vacuum to afford A7 2-[3,5-dichloro-4-[(4-hydroxy-3-isopropyl-phenyl)methyl]phenoxy]acetic acid (22 g, 81% yield) as a white solid. TLC: DCM/MeOH=20/1; Rf=0.2. $^1H$ NMR (400 MHz, DMSO-d6) δ 9.06 (s, 1H), 7.09 (s, 2H), 6.98 (d, J=1.7 Hz, 1H), 6.67 (dd, J=8.3, 2.1 Hz, 1H), 6.64 (d, J=8.2 Hz, 1H), 4.75 (s, 2H), 4.04 (s, 2H), 3.14-3.08 (m, 1H), 1.10 (d, J=6.9 Hz, 6H).

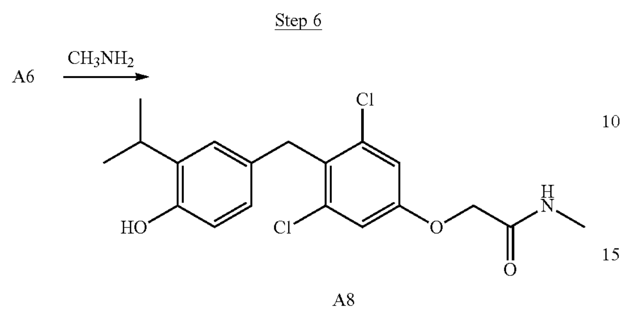

A8

A solution of A6 methyl 2-[3,5-dichloro-4-[(4-hydroxy-3-isopropyl-phenyl)methyl]phenoxy]acetate (6.0 g, 16 mmol) in THF (10 mL) and methylamine (30 mL, 40% in water) in a sealed tube was stirred at 70° C. overnight. The mixture was cooled down to rt and water (30 mL) was added. The mixture was extracted with EtOAc (20 mL×2), and the combined organic phase was washed by brine (30 mL), dried over $Na_2SO_4$ and concentrated in vacuo. The residue was washed with n-hexane/EtOAc=10/1 (30 mL), and the resulting solid was filtered and dried to afford A8 N-methyl 2-[3,5-dichloro-4-[(4-hydroxy-3-isopropyl-phenyl)methyl]phenoxy]acetamide (5.0 g, 84% yield) as a light brown solid. TLC: DCM/MeOH=20/1, Rf=0.18. $^1$HNMR (400 MHz, DMSO-d6) δ 9.08 (s, 1H), 8.06 (s, 1H), 7.14 (s, 2H), 6.98 (d, J=2.1 Hz, 1H), 6.69-6.62 (m, 2H), 4.54 (s, 2H), 4.04 (s, 2H), 3.17-3.07 (m, 1H), 2.65 (d, J=4.6 Hz, 3H), 1.10 (d, J=6.9 Hz, 6H).

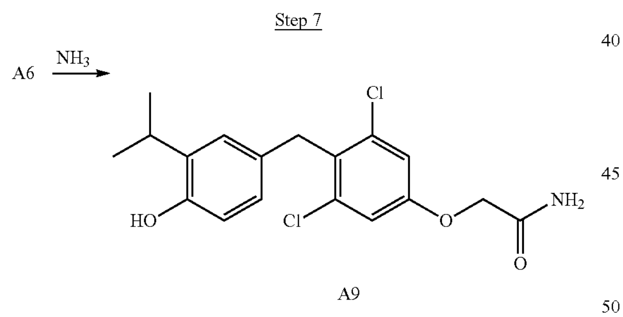

A9

A solution of A6 methyl 2-[3,5-dichloro-4-[(4-hydroxy-3-isopropyl-phenyl)methyl]phenoxy]acetate (200 mg, 0.52 mmol) in THF (2 mL) and $NH_3$—$H_2O$ (5 mL) in a sealed tube was stirred at 70° C. overnight. The mixture was cooled down to rt and water (10 mL) was added. The mixture was then extracted with EtOAc (10 mL×2). The combined organic phase was washed by brine (30 mL), dried over $Na_2SO_4$ and concentrated in vacuum. Reverse-phase column purification afforded A9 2-[3,5-dichloro-4-[(4-hydroxy-3-isopropyl-phenyl)methyl]phenoxy]acetatamide (110 mg, 57% yield) as a light brown solid. TLC: DCM/MeOH=20/1; Rf=0.17. $^1$HNMR: 1HNMR (400 MHz, DMSO-d6) δ 9.09 (s, 1H), 7.58 (s, 1H), 7.42 (s, 1H), 7.12 (s, 2H), 6.98 (s, 1H), 6.68-6.62 (m, 2H), 4.50 (s, 2H), 4.04 (s, 2H), 3.13 (q, J=6.9 Hz, 1H), 1.10 (d, J=6.9 Hz, 6H).

Example 1: 2-(3,5-dichloro-4-(4-hydroxy-3-(propan-2-yl-d7)benzyl)phenoxy)-N-methylacetamide (Compound 1)

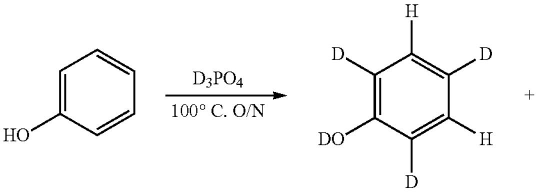

A-10

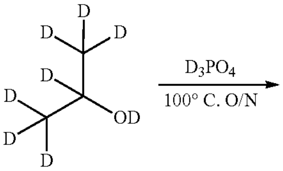

A-11

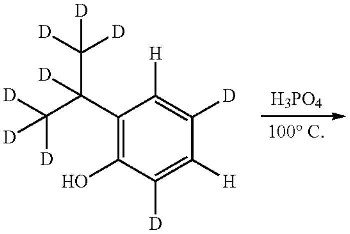

A-12

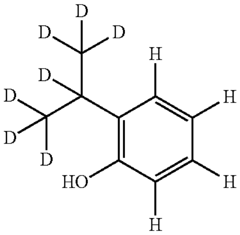

A-13

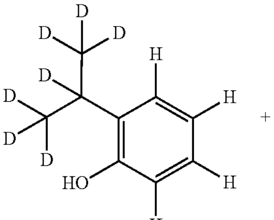

A-13

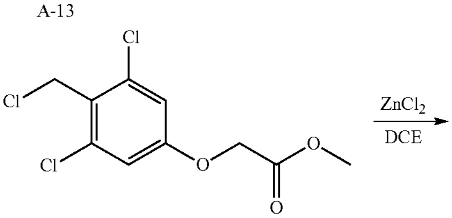

A-4

-continued

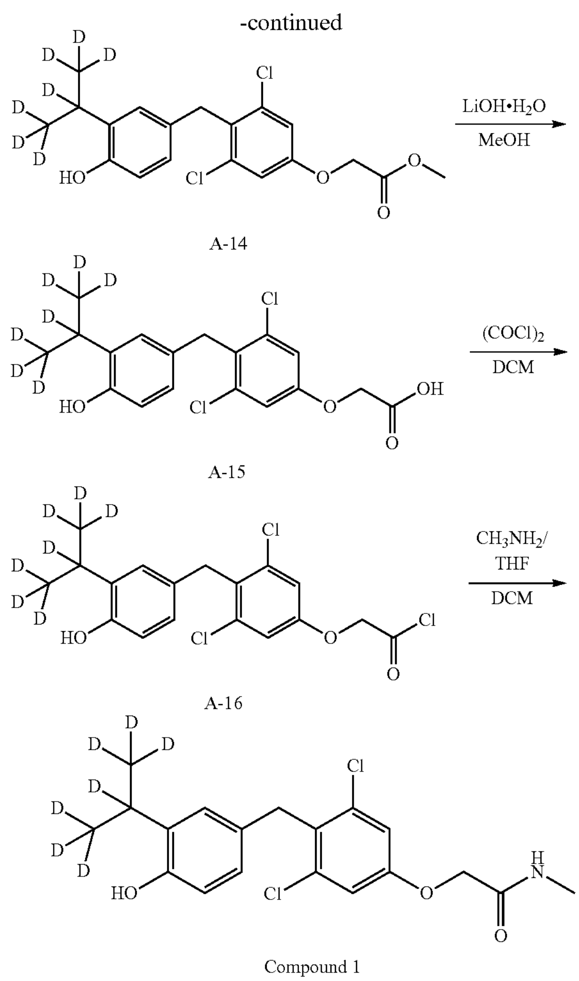

A-14

A-15

A-16

Compound 1

A solution of phenol (6.0 g, 63.75 mmol, 5.60 mL) in $D_3PO_4$ (60 mL) was stirred at 100° C. overnight. The mixture was diluted with $D_2O$ (30 mL) and extracted with CDCl3 (20 mL*2). The combined organic layer was concentrated in vacuum to afford A-10 (5.2 g, 84.0% yield) as a yellow oil. $^1$HNMR (400 MHz, DMSO-$d_6$) δ 9.31 (s, 1H), 7.15 (s, 2H)

To a solution of A-10 (2.2 g, 22.65 mmol) in $D_3PO_4$ (22 mL) at rt was added A-11 (1.7 g, 24.92 mmol). The mixture was stirred at 100° C. overnight. The reaction mixture was diluted with $H_2O$ (80 mL), extracted with EtOAc (30 mL*2). The combined organic phase was washed by brine (30 mL*2), dried over $Na_2SO_4$, concentrated in vacuum and purified by RP column and silica gel column (Pet.ether/EtOAc=100/1-20/1) to afford A-12 (910 mg, 27.7% yield) as a colorless oil. $^1$HNMR (400 MHz, DMSO-$d_6$) δ 9.17 (s, 1H), 7.09 (d, J=1.2 Hz, 1H), 6.95 (d, J=1.2 Hz, 1H).

To a solution of A-12 (900 mg, 6.20 mmol) in $H_3PO_4$ (20 mL) was stirred at 100° C. 2d. The reaction mixture was diluted with $H_2O$ (50 mL), extracted with EtOAc (30 mL*2). The combined organic phase was washed by brine (20 mL*2), dried over $Na_2SO_4$, concentrated in vacuum to afford A-13 (780 mg, 87.9% yield) as a yellow oil. $^1$H NMR (400 MHz, DMSO-$d_6$) δ 9.17 (s, 1H), 7.09 (dd, J=7.6, 1.6 Hz, 1H), 6.96 (m, 1H), 6.73 (m, 2H).

To a solution of A-4 (772 mg, 2.72 mmol) in DCE (3 mL) at RT was added A-13 (780 mg, 5.45 mmol) and $ZnCl_2$ (1 M, 6.8 mL). The reaction was heated to 85° C. and stirred overnight. The reaction mixture was diluted with water (50 mL), extracted with DCM (30 mL*3). The combine organic phases was washed with brine (20 mL*2), dried over $Na_2SO_4$, concentrated under reduce pressure. The crude product was purified by silica gel column (pet.ether/EtOAc=50/1 to 10/1) to afford A-14 (460 mg, 43.3% yield) as a yellow solid. $^1$H NMR (400 MHz, DMSO-$d_6$) δ 9.07 (s, 1H), 7.14 (s, 2H), 6.97 (d, J=1.6 Hz, 1H), 6.67 (dd, J=8.0, 2.0 Hz, 1H), 6.63 (d, J=8.4 Hz, 1H), 4.89 (s, 2H), 4.04 (s, 2H), 3.70 (s, 2H).

To a mixture of A-14 (460 mg, 1.18 mmol) in MeOH (3 mL) and $H_2O$ (1 mL) was added LiOH·$H_2O$ (148 mg, 3.54 mmol). The mixture was stirred at RT for 1 h. The mixture was adjusted pH=4-5 with 1 N HCl and extracted with EtOAc (20 mL*2). The combined organic phase was washed by brine (20 mL*2), dried over $Na_2SO_4$, concentrated in vacuum and purified by prep-HPLC to afford A-15 (110 mg, 24.6% yield) as a white solid. LCMS: T=1.250 min, [M−1]=374.00. $^1$H NMR (400 MHz, DMSO-$d_6$) δ 13.10 (s, 1H), 9.07 (s, 1H), 7.10 (s, 2H), 6.97 (d, J=2.0 Hz, 1H), 6.67 (dd, J=8.4, 2.0 Hz, 1H), 6.63 (d, J=8.0 Hz, 1H), 4.77 (s, 2H), 4.04 (s, 2H).

To a solution of A-15 (200 mg, 0.53 mmol) in DCM (2 mL) was added $(COCl)_2$ (101 mg, 0.80 mmol) and DMF (Cat.). The mixture was stirred at RT for 1 h. The mixture was concentrated to dryness to afford A-16 (200 mg, 95.3% yield) as a colorless oil.

To a solution of A-16 (200 mg, 0.51 mmol) in DCM (2 mL) was added $CH_3NH_2$/THF (2 M, 2 mL). The mixture was stirred at RT for 1 h. The mixture was diluted with water (20 mL) and extracted with EtOAc (20 mL). The organic phase was washed by brine (30 mL), dried over $Na_2SO_4$, concentrated in vacuum and purified by prep-HPLC to afford Compound 1 (100 mg, 50.2% yield) as a white solid. LCMS: T=3.050 min, [M−1]=387.20. $^1$H NMR (400 MHz, DMSO-$d_6$) δ 9.07 (s, 1H), 8.06 (d, J=4.8 Hz, 1H), 7.14 (s, 2H), 6.97 (d, J=1.6 Hz, 1H), 6.67 (dd, J=8.4, 2.0 Hz, 1H), 6.63 (d, J=8.0 Hz, 1H), 4.54 (s, 2H), 4.04 (s, 2H), 2.65 (d, J=4.4 Hz, 3H).

Example 2: Synthesis of 2-(3,5-dichloro-4-(hydroxy-3-(propan-2-yl-d7)benzyl)phenoxy)acetic Acid (Compound 2)

(Compound 2)

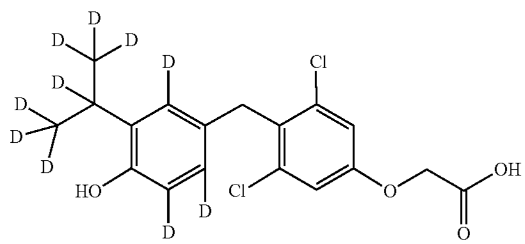

Compound 2 was prepared in the same fashion as A7 substituting 2-iso-propylphenol-$d_{12}$ for A5 in Example A, Step 4. LCMS: T=1.527 min, [M−1]=376.1. $^1$H NMR (400 MHz, DMSO-$d_6$) δ 13.09 (s, 1H), 9.05 (s, 1H), 7.10 (d, J=1.2 Hz, 2H), 6.64 (s, 1H), 4.77 (s, 2H), 4.04 (s, 2H).

Example 3: Synthesis of 2-(3,5-dichloro-4-(hydroxy-3-(propan-2-yl-d7)benzyl)phenoxy)acetamide (Compound 3)

(Compound 3)

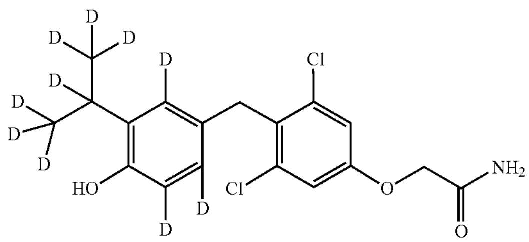

Compound 3 was prepared in the same fashion as A9 substituting 2-iso-propylphenol-$d_{12}$ for A5 in Example A, Step 4. LCMS: T=1.347 min, [M−1]=376.1.

Example 4: Synthesis of 2-(3,5-dichloro-4-((4-hydroxy-3-isopropylphenyl)methyl-d2)phenoxy)acetic Acid (Compound 4)

(Compound 4)

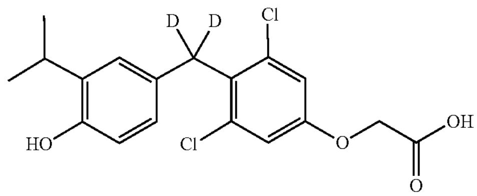

Compound 4 was prepared in the same fashion as A7 substituting 20% aqueous formalin-$d_2$ for 36% aqueous formaldehyde in Example A, Step 1. LCMS: T=1.314 min, [M−1]=369.0. $^1$H NMR (400 MHz, DMSO-$d_6$) δ 9.08 (s, 1H), 7.06 (s, 2H), 6.98 (d, J=2.0 Hz, 1H), 6.67 (dd, J=8.0, 2.0 Hz, 1H), 6.64 (d, J=8.0 Hz, 1H), 4.67 (s, 2H), 3.16-3.09 (m, 1H), 1.10 (d, J=6.8 Hz, 6H).

Example 5: Synthesis of 2-(3,5-dichloro-4-((4-hydroxy-3-isopropylphenyl)methyl-d2)phenoxy)acetamide (Compound 5)

(Compound 5)

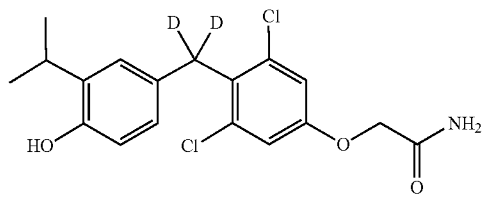

Compound 5 was prepared in the same fashion as A9 substituting 20% aqueous formalin-$d_2$ for 36% aqueous formaldehyde in Example A, Step 1. LCMS: T=1.042 min, [M−1]=368.0. $^1$H NMR (400 MHz, DMSO-$d_6$) δ 9.06 (s, 1H), 7.56 (s, 1H), 7.40 (s, 1H), 7.12 (s, 2H), 6.98 (d, J=2.0 Hz, 1H), 6.67 (dd, J=8.0, 2.0 Hz, 1H), 6.64 (d, J=8.0 Hz, 1H), 4.50 (s, 2H), 3.13 (p, J=6.8 Hz, 1H), 1.11 (d, J=6.8 Hz, 6H).

Example 6: Synthesis of 2-(3,5-dichloro-4-(4-hydroxy-3-isopropylbenzyl)phenoxy-2,6-d2)acetic Acid (Compound 6)

(Compound 6)

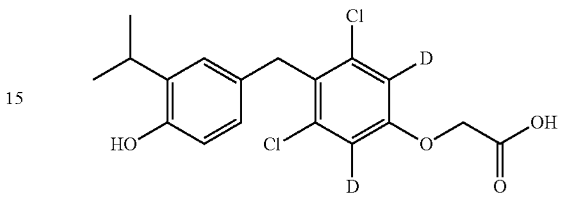

Compound 6 was prepared in the same fashion as A7 substituting 3,5-dichlorophenol-2,4,6-$d_3$ for A1 in Example A, Step 1. LCMS: T=1.210 min, [M−1]=369.1. $^1$H NMR (400 MHz, DMSO-$d_6$) δ 13.05 (s, 1H), 9.06 (s, 1H), 6.98 (d, J=2.0 Hz, 1H), 6.67 (dd, J=8.2, 2.1 Hz, 1H), 6.64 (d, J=8.2 Hz, 1H), 4.76 (s, 2H), 4.04 (s, 2H), 3.18-3.07 (m, 1H), 1.10 (d, J=6.9 Hz, 6H).

Example 7: Synthesis of 2-(3,5-dichloro-4-(4-hydroxy-3-isopropylbenzyl)phenoxy-2,6-d2)acetamide (Compound 7)

(Compound 7)

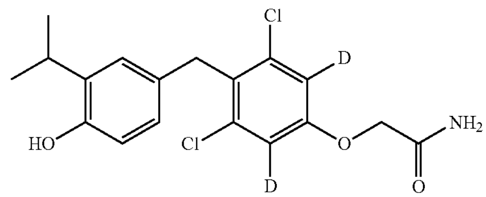

Compound 7 was prepared in the same fashion as A9 substituting 3,5-dichlorophenol-2,4,6-$d_3$ for A1 in Example A, Step 1. LCMS: T=1.054 min, [M−1]=368.1. $^1$H NMR (400 MHz, DMSO-$d_6$) δ 9.06 (s, 1H), 7.56 (s, 1H), 7.40 (s, 1H), 6.98 (d, J=2.0 Hz, 1H), 6.70-6.60 (m, 2H), 4.50 (s, 2H), 4.04 (s, 2H), 3.13 (p, J=6.9 Hz, 1H), 1.10 (d, J=7.0 Hz, 6H).

Example 8: Synthesis of 2-(3,5-dichloro-4-(4-hydroxy-3-isopropylbenzyl)phenoxy)acetic-2,2-d2 Acid (Compound 8)

(Compound 8)

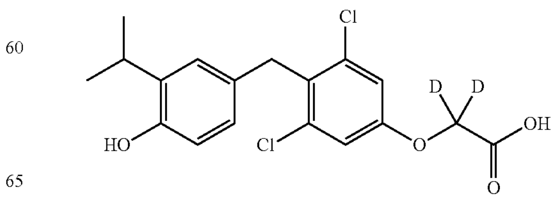

Compound 8 was prepared in the same fashion as A7 substituting methyl bromoacetate-2,2-$d_2$ for methyl chloroacetate in Example A, Step 2. LCMS: T=1.340 min, [M−1]=369.1. $^1$H NMR (400 MHz, DMSO-$d_6$) δ 9.07 (s, 1H), 7.09 (s, 2H), 6.98 (s, 1H), 6.72-6.57 (m, 2H), 4.04 (s, 2H), 3.15-3.07 (m, 1H), 1.10 (d, J=7.2 Hz, 6H).

Example 9: Synthesis of 2-(3,5-dichloro-4-(4-hydroxy-3-isopropylbenzyl)phenoxy)acetamide-2,2-d2 (Compound 9)

(Compound 9)

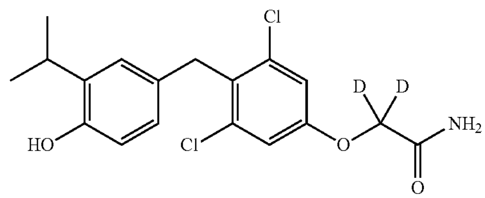

Compound 9 was prepared in the same fashion as A9 substituting methyl bromoacetate-2,2-$d_2$ for methyl chloroacetate in Example A, Step 2. LCMS: T=1.089 min, [M+1]=370.1. $^1$H NMR (400 MHz, DMSO-$d_6$) δ 9.06 (s, 1H), 7.56 (s, 1H), 7.44-7.36 (m, 1H), 7.12 (s, 2H), 6.98 (d, J=2.0 Hz, 1H), 6.67 (dd, J=8.4, 2.4 Hz, 1H), 6.63 (d, J=8.4 Hz, 1H), 4.04 (s, 2H), 3.13 (m, 1H), 1.11 (d, J=7.2 Hz, 6H).

Example 10: Synthesis of 2-(4-(hydroxy-3-(propan-2-yl-d7)benzyl)-3,5-dimethylphenoxy)acetic Acid (Compound 10)

(Compound 10)

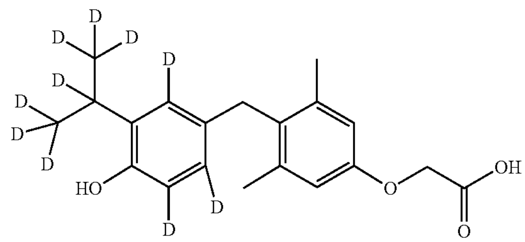

Compound 10 was prepared in the same fashion as A7 by substituting 3,5-dimethylphenol for 3,5-dichlorophenol in Example A, Step 1, and by substituting 2-iso-propylphenol-$d_{12}$ for A5 in Example A, Step 4. LCMS: T=2.035 min, [M−1]=339.2. $^1$H NMR (400 MHz, DMSO-$d_6$) δ 8.95 (s, 1H), 6.61 (d, J=4.4 Hz, 1H), 4.60 (s, 2H), 3.79 (s, 2H), 2.15 (s, 6H).

Example 11: Synthesis of 2-(4-(hydroxy-3-(propan-2-yl-d7)benzyl)-3,5-dimethylphenoxy)-N-methylacetamide (Compound 11)

(Compound 11)

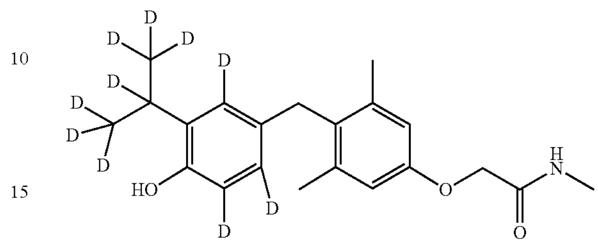

Compound 11 was prepared in the same fashion as A8 by substituting 3,5-dimethylphenol for 3,5-dichlorophenol in Example A, Step 1, and by substituting 2-iso-propylphenol-$d_{12}$ for A5 in Example A, Step 4. LCMS: T=2.363 min, [M+1]=352.2. $^1$H NMR (400 MHz, DMSO-$d_6$) δ 8.96 (s, 1H), 7.95 (s, 1H), 6.66 (s, 1H), 6.60 (s, 1H), 4.40 (s, 2H), 3.79 (s, 2H), 2.65 (d, J=4.4 Hz, 3H), 2.16 (s, 6H).

Example 12: Synthesis of 2-(4-((4-hydroxy-3-isopropylphenyl)methyl-d2)-3,5-dimethylphenoxy) acetic Acid (Compound 12)

(Compound 12)

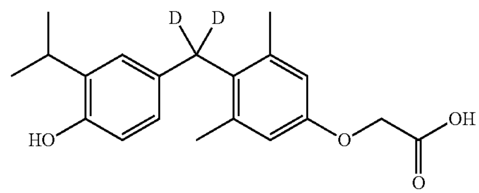

Compound 12 was prepared in the same fashion as A7 by substituting both 20% aqueous formalin-$d_2$ for 36% aqueous formaldehyde and 3,5-dimethylphenol for 3,5-dichlorophenol in Example A, Step 1. LCMS: T=1.122 min, [M−1]=329.1. $^1$H NMR (400 MHz, DMSO-$d_6$) δ 12.88 (s, 1H), 8.95 (s, 1H), 6.85 (d, J=2.4 Hz, 1H), 6.60 (d, J=8.0 Hz, 3H), 6.45 (dd, J=8.4, 2.4 Hz, 1H), 4.60 (s, 2H), 3.12 (p, J=6.8 Hz, 1H), 2.15 (s, 6H), 1.10 (d, J=6.8 Hz, 6H).

Example 13: Synthesis of 2-(4-((4-hydroxy-3-isopropylphenyl)methyl-d2)-3,5-dimethylphenoxy)-N-methylacetamide (Compound 13)

(Compound 13)

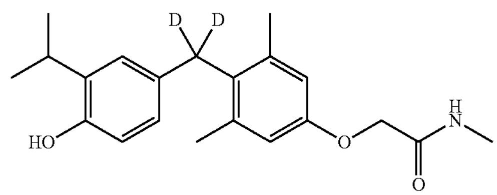

Compound 13 was prepared in the same fashion as A8 by substituting both 20% aqueous formalin-$d_2$ for 36% aqueous formaldehyde and 3,5-dimethylphenol for 3,5-dichlorophenol in Example A, Step 1. LCMS: T=1.205 min, [M−1]=342.2. $^1$H NMR (400 MHz, DMSO-$d_6$) δ 8.97 (s, 1H), 7.96 (d, J=4.8 Hz, 1H), 6.84 (d, J=2.4 Hz, 1H), 6.66 (s, 2H), 6.60 (d, J=8.0 Hz, 1H), 6.45 (dd, J=8.4, 2.4 Hz, 1H), 4.40 (s, 2H), 3.12 (p, J=6.8 Hz, 1H), 2.65 (d, J=4.8 Hz, 3H), 2.16 (s, 6H), 1.09 (d, J=6.8 Hz, 6H).

Example 14: Synthesis of 2-(4-(4-hydroxy-3-isopropylbenzyl)-3,5-bis(methyl-d3)phenoxy-2,6-d2)acetic acid (Compound 14)

(Compound 14)

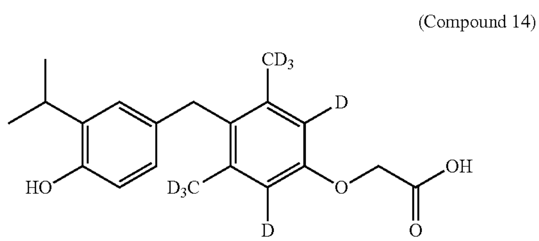 [SMILES: [2H]c1c(OCC(=O)O)c([2H])c(C([2H])([2H])[2H])c(Cc2ccc(O)c(C(C)C)c2)c1C([2H])([2H])[2H]]

Compound 14 was prepared in the same fashion as A7 substituting 3,5-dimethylphenol-2,4,6-$d_{10}$ for A1 in Example A, Step 1. LCMS: T=1.019 min, [M−1]=333.1. $^1$H NMR (400 MHz, DMSO-$d_6$) δ 12.77 (s, 1H), 8.97 (s, 1H), 6.85 (d, J=2.2 Hz, 1H), 6.60 (d, J=8.2 Hz, 3H), 6.44 (dd, J=8.2, 2.3 Hz, 1H), 4.60 (s, 2H), 3.78 (s, 2H), 3.15-3.06 (m, 1H), 1.10 (d, J=6.9 Hz, 6H).

Example 15: Synthesis of 2-(4-(4-hydroxy-3-isopropylbenzyl)-3,5-bis(methyl-d3)phenoxy-2,6-d2)-N-methylacetamide (Compound 15)

(Compound 15)

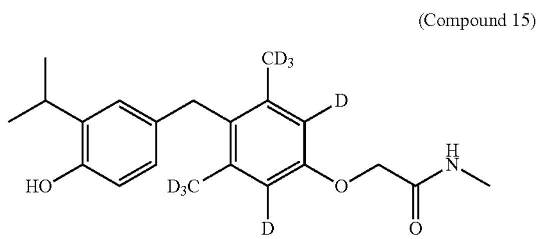 [SMILES: [2H]c1c(OCC(=O)NC)c([2H])c(C([2H])([2H])[2H])c(Cc2ccc(O)c(C(C)C)c2)c1C([2H])([2H])[2H]]

Compound 15 was prepared in the same fashion as A8 substituting 3,5-dimethylphenol-2,4,6-$d_{10}$ for A1 in Example A, Step 1. LCMS: T=1.005 min, [M−1]=346.2. $^1$H NMR (400 MHz, DMSO-$d_6$) δ 8.97 (s, 1H), 7.96 (s, 1H), 6.84 (d, J=2.2 Hz, 1H), 6.66 (s, 2H), 6.60 (d, J=8.2 Hz, 1H), 6.45 (dd, J=8.1, 2.3 Hz, 1H), 4.40 (s, 2H), 3.79 (s, 2H), 3.12 (p, J=6.9 Hz, 1H), 2.65 (d, J=4.7 Hz, 3H), 1.09 (d, J=6.9 Hz, 6H).

Example 16: Synthesis of 2-(4-(4-hydroxy-3-isopropylbenzyl)-3,5-bis(methyl-d3)phenoxy-2,6-d2)-N-methylacetamide (Compound 16)

(Compound 16)

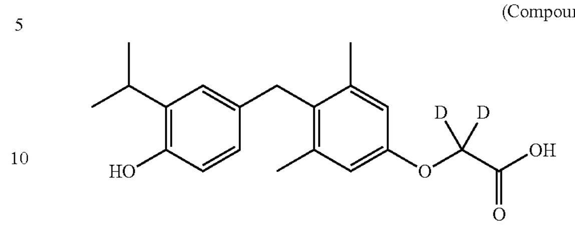

Compound 16 was prepared in the same fashion as A7 substituting 3,5-dimethylphenol for 3,5-dichlorophenol in Example A, Step 1, and substituting methyl bromoacetate-2,2-$d_2$ for methyl chloroacetate in Example A, Step 2. LCMS: T=1.089 min, [M−1]=329.2. $^1$H NMR (400 MHz, DMSO-$d_6$) δ 8.96 (s, 1H), 6.85 (d, J=2.1 Hz, 1H), 6.61 (d, J=8.1 Hz, 1H), 6.59 (s, 2H), 6.45 (dd, J=8.4, 2.4 Hz, 1H), 3.79 (s, 2H), 3.12 (p, J=7.2 Hz, 1H), 2.15 (s, 6H), 1.10 (d, J=7.2 Hz, 6H).

Example 17: Synthesis of 2-(4-(4-hydroxy-3-isopropylbenzyl)-3,5-dimethylphenoxy)-N-methylacetamide-2,2-d2 (Compound 17)

(Compound 17)

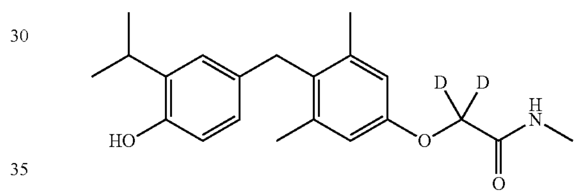

Compound 17 was prepared in the same fashion as A8 substituting 3,5-dimethylphenol for 3,5-dichlorophenol in Example A, Step 1, and substituting methyl bromoacetate-2,2-$d_2$ for methyl chloroacetate in Example A, Step 2. LCMS: T=0.940 min, [M+1]=344.1. $^1$H NMR (400 MHz, DMSO-$d_6$) δ 8.96 (s, 1H), 7.95 (d, J=5.5 Hz, 1H), 6.84 (d, J=2.2 Hz, 1H), 6.66 (s, 2H), 6.60 (d, J=8.2 Hz, 1H), 6.45 (dd, J=8.2, 2.2 Hz, 1H), 3.79 (s, 2H), 3.16-3.08 (m, 1H), 2.65 (d, J=4.7 Hz, 3H), 2.16 (s, 6H).

Example 18: Synthesis of 2-(3,5-dichloro-4-(hydroxy-3-(propan-2-yl-d7)benzyl)phenoxy)acetic acid (Compound 18)

(Compound 18)

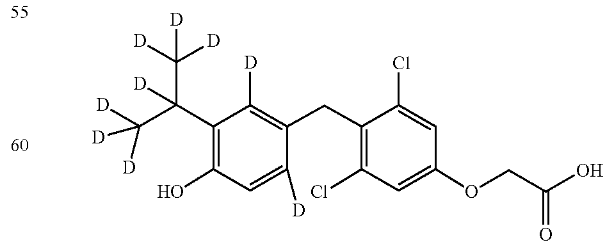

Compound 18 was prepared in the same fashion as A7 substituting 2-iso-propylphenol-do for A5 in Example A, Step 4. LCMS: T=1.541 min, [M−1]=377.1. $^1$H NMR (400 MHz, DMSO-$d_6$) δ 13.09 (s, 1H), 9.05 (s, 1H), 7.10 (s, 2H), 4.77 (s, 2H), 4.04 (s, 2H).

Example 19: Synthesis of 2-(3,5-dichloro-4-(hydroxy-3-(propan-2-yl-d7)benzyl)phenoxy)acetamide (Compound 19)

(Compound 19)

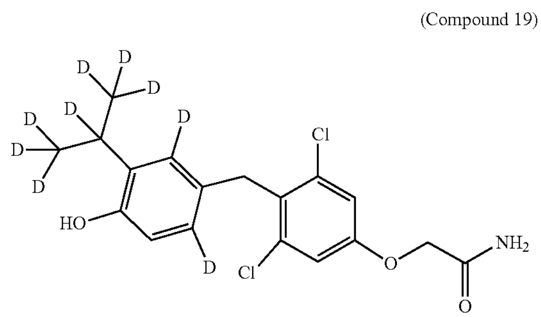 [SMILES: [2H]c1cc(O)c(C([2H])(C([2H])([2H])[2H])C([2H])([2H])[2H])c([2H])c1Cc1c(Cl)cc(OCC(N)=O)cc1Cl]

Compound 19 is prepared in the same fashion as A9 substituting 2-iso-propylphenol-d9 for A5 in Step 4 in Scheme 3.

Example 20: Synthesis of 2-(3,5-dichloro-4-(hydroxy-3-(propan-2-yl-d7)benzyl)phenoxy)-N-methylacetamide (Compound 20)

(Compound 20)

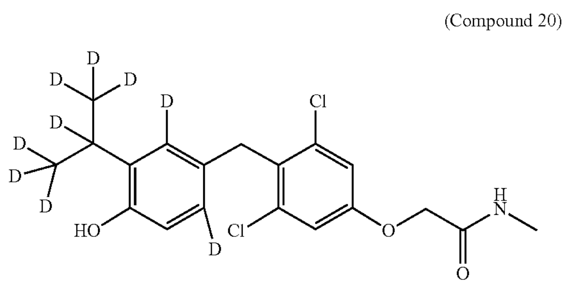 [SMILES: [2H]c1cc(O)c(C([2H])(C([2H])([2H])[2H])C([2H])([2H])[2H])c([2H])c1Cc1c(Cl)cc(OCC(=O)NC)cc1Cl]

Compound 20 is prepared in the same fashion as A9 substituting 2-iso-propylphenol-$d_9$ for A5 in Example A, Step 4.

Example 21: Assays

FAAH Substrate Evaluation

Purified recombinant human FAAH (rhFAAH) was purchased from Cayman Chemical (Ann Arbor, MI, USA). The total volume for each incubation was 400 μL containing a final 0.5 ng/μL rhFAAH, 1 μM test compound, 1.25% ethanol or 1 μM PF-3845 (FAAH inhibitor), and 0.1% bovine serum albumin in Tris-EDTA buffer at pH 8.0). The positive control was LL-341001. The incubation was conducted at the room temperature. At 0, 5, 15, 30 and 60 minutes, an aliquot of 30 μL reaction mixtures was removed and mixed with 300 μL acetonitrile containing 5 ng/mL terfenadine and 10 ng/mL tolbutamide as internal standards to quench the reaction. The resulting mixture was centrifuged at 4000 rpm, 4° C. for 15 minutes, and 100 μL supernatant was ready for LC-MS/MS analysis to measure the formation of acid metabolite.

LC-MS/MS Analysis

Acquity Ultra Performance LC system from Waters was used for sample analysis. The chromatography was performed on a reverse phase Kinetex 2.6 μm C18 column, 2.1×30 mm, 100 Å. The mobile phase A comprised of 0.1% formic acid in water and mobile phase B comprised of 0.1% formic acid in acetonitrile with a 2-min run time at the flow rate of 0.8 mL/min for the acid metabolite from positive control or a 1.5 min run time at the flow rate of 0.9 mL/min for the acid metabolite of test compounds. The mass spectrometer (API-5500 and API Q Trap 4000 Applied Biosystems/MDS SCIEX Instruments, Framingham, MA, USA) was operated under ESI positive or negative ion MRM mode.

Data Analysis

The formation of acid metabolite was monitored and quantified using one calibration point of 1 μM. The observed rate constant (ke) for the acid metabolite formation was calculated by plotting the metabolite concentration versus time of incubation with the slope being ke and is shown in Table 1.

TABLE 1

| Compound | ke | Compound | ke | Compound | ke |
|---|---|---|---|---|---|
| 1 | A | 5 | A | 7 | A |
| 9 | A | 11 | A | 13 | A |
| 15 | A | 17 | A | | |

A = ke is less than 3.0 and more than or equal to 0.1.

Transactivation Assay

Human epithelial kidney cells (HEK 293) were grown to 80% confluency in Dubelcco's modified Eagles 4.5 g/L glucose medium (high glucose DMEM) containing 10% fetal bovine serum, 50 units/mL penicillin and 50 μg/mL streptomycin. The cells were trypsinized with 0.25% trypsin, then diluted to $5\times10^5$ cells/mL with high glucose DMEM. Cells were added to Costar 3917 96-well plates at $5\times10^4$ cells/well, then incubated at 37° C. for 24 hours. 1.5 μg of TR expression vector (full length TRα-CMV or TRβ-CMV), 1.5 μg of a reporter plasmid containing a DR4 thyroid hormone response element (TRE) direct repeat spaced by four nucleotides (AGGTCAcaggAGGTCA) cloned upstream of a minimal thymidine kinase promoter linked to a firefly luciferase coding sequence, and 0.75 μg of a pRL-SV40 constitutive *Renilla* luciferase reporter plasmid were diluted into 540 μl of OptiMEM. 27 μL of lipofectamine reagent was diluted into 540 μL of OptiMEM. The plasmid and lipofectamine dilutions were combined then incubated at RT for 10 min. The mixture was then diluted into 4.29 mL of OptiMEM. Plates were washed with 100 μL of phosphate buffered saline (PBS) at pH 7.2 without magnesium or calcium chloride per well. Transfection mixtures were added at 50 μL per well, then incubated at 37° C. for 4 hours. Modified DME/F-12 Ham's medium without phenol red containing 15 mM HEPES and bicarbonate, 5 mM L-glutamine, charcoal-stripped FBS, 50 units/mL penicillin and 50 μg/mL streptomycin was added at 50 μL per well, then the plates were incubated at 37° C. for 20 hours. Drug stocks were made at 10 mM in DMSO, then serially diluted to 1× concentrations in DME/F-12 Ham's. Plates were washed with 100 μL of PBS (pH 7.2) per well. 100 μL of each drug stock was added to the wells in triplicate, and then the plates are incubated at 37° C. for 24 hours.

Cells were assayed for luciferase activity using the Promega DualGlo kit. 50 μl of Luciferase Reagent was added per well, the plate was rocked for 15 min at RT, and then the plate was read for firefly luciferase activity. A 50 μl volume of Stop & Glo Reagent was added per well, then the plate was read for *Renilla* luciferase activity. Data normalized to *Renilla* internal control are analyzed with GraphPad Prism v.4a using the sigmoid dose response model to generate $EC_{50}$ values ±SEM, which are shown in Table 2.

TABLE 2

| Compound | TRα $EC_{50}$ | TRβ $EC_{50}$ |
|---|---|---|
| A-15 | A | A |
| 2 | A | A |
| 4 | A | A |
| 6 | A | A |
| 8 | A | A |
| 10 | A | A |
| 12 | A | A |
| 14 | A | A |
| 16 | A | A |
| 18 | A | A |

A = $EC_{50}$ is less than 1.0 μM and more than or equal to 0.001 μM.

Animal Studies

Experimental protocols are in compliance with the National Institutes of Health Guide for the Care and Use of Laboratory Animals and approved by the Oregon Health & Science University Institutional Animal Care & Use Committee. Wild type male C57BL/6J mice, aged 8-10 weeks, are housed in a climate controlled room with a 12 hour light-dark cycle with ad libitum access to food and water.

Distribution Studies

Mice are injected once intraperitoneally (ip) with GC-1 at 9.14 μmol/kg, and analogs at 0.914, 9.14, and 30.5 μmol/kg. Euthanasia was performed on three mice per dose at 1 hr and the tissues and blood are harvested. Tissues are immediately frozen and blood was kept on ice for a minimum of 30 minutes and then spun down at 7,500×G for 15 minutes. Serum (100 μL) was collected and was stored with tissues at −80° C. until samples are processed.

Serum Processing

The serum samples are warmed to RT and 10 uL of 2.99 μM internal standard (D6-GC-1) was added to them. Acetonitrile (500 uL) was added and the sample was vortexed for 20 seconds. The sample was then centrifuged at 10,000×G for 15 minutes at 4° C. Next, 90% of the upper supernatant was transferred to a glass test tube and concentrated using a speedvac for 1.5 hr at 45° C. The dried sample was then dissolved in 400 μL of 50:50 ACN:$H_2O$ and vortexed for 20 seconds. The resulting mixture was transferred to an Eppendorf tube and centrifuged at 10,000×G for 15 minutes. The supernatant was filtered with 0.22 μM centrifugal filters and submitted for LCMS/MS analysis. The standard curve was made with 100 μL of serum from a 8-10 week old mouse not injected with T3, GC-1, or analogs. The processing was performed exactly the same except after filtering the sample was split among 6 vials. GC-1, JD-20, and JD-21 are added to 5 of the 6 vials to make final concentrations of each compound in matrix of (0.1 pg/μL, 1 pg/μL, 10 pg/μL, 100 pg/μL, and 1000 pg/μL).

Brain Processing

The brain samples are warmed to RT and transferred to a homogenizer tube with 5 GoldSpec 1/8 chrome steel balls (Applied Industrial Technologies). The resulting tube was weighed and then 1 mL of $H_2O$ was added, followed by 10 μL of 2.99 μM internal standard (D6-Sobetirome). The tube was homogenized with a Bead Bug for 30 seconds and then transferred to a Falcon® tube containing 3 mL of ACN. A 1 ml volume of ACN was used to wash the homogenizer tube. Then the solution was transferred back to the Falcon® tube. The sample was then processed using the same method for the serum processing described above except the sample was concentrated in a glass tube using a speed vac for 4 hr at 45° C.

Gene Activation

Mice are injected once intraperitoneally (ip) with vehicle (1:1 saline/DMSO), T3 at 0.305 μmol/kg, GC-1 at 9.14 μmol/kg, and analogs at 0.914, 9.14, and 30.5 μmol/kg. Euthanasia was performed on three mice per dose at 2 hr and the tissues are harvested. The brain tissues collected for qPCR analysis are processed according to a protocol for RNA extraction using Trizol reagent and the PureLink RNA mini kit, using Qiagen RNase-free DNase kit during the optional DNase treatment step. 1 μg of extracted RNA was used to synthesize cDNA via a reverse transcription (RT) reaction using the Qiagen Quanti Tect Reverse Transcription kit. DNA contamination was controlled for by duplicating one sample without the addition of RT enzyme. Expression of the Hairless (Hr) gene was measured by QPCR using the QuantiTect SYBR green PCR kit from Qiagen. The primer sequences for hairless (Fwd: CCAAGTCTGGGCCAAGTTTG; Rev: TGTCCTTGGTCCGATTGGAA) are previously described by *Barca*-Mayo19. The template cDNA was diluted 2-fold to minimize the interference of RT reagents in the qPCR reaction. Glyceraldehyde-3-Phosphate Dehydrogenase (GAPDH) was the housekeeping gene used for normalizing between samples. Data analysis for single dose experiment was done using the comparative CT method to look at the relative differences in Hr gene expression. Data analysis for dose-response experiment was done using GraphPad Prism v.4a with the sigmoid dose response model to generate $EC_{50}$ values ±SEM.

Chemistry General

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A compound having the structure of Formula (VI):

(VI)

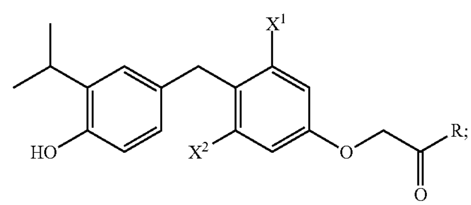

or a pharmaceutically acceptable salt or solvate thereof;

wherein

R is OH or $OR^1$;

$X^1$ and $X^2$ are each independently halo;

$R^1$ is alkyl, alkenyl, alkynyl, carbocycle, carbocyclealkyl, heterocycle or heterocyclealkyl, wherein each alkyl, carbocycle, carbocyclealkyl, heterocycle or heterocyclealkyl is optionally substituted with one or more of halo, cyano, $—OR^a$, $—NR^aR^b$, $—S(O)_2R^a$ or $—S(O)_2OR^a$;

each occurrence of halo is independently chloro, bromo, fluoro or iodo; and $R^a$ and $R^b$ is independently hydrogen or alkyl;

and wherein at least one hydrogen atom of the compound of Formula (VI) is replaced with deuterium.

2. The compound of claim 1, or a pharmaceutically acceptable salt or solvate thereof, wherein R is OH.

3. The compound of claim 2, or a pharmaceutically acceptable salt or solvate thereof, wherein $X^1$ and $X^2$ are chloro.

4. A compound having one of the following structures, or a pharmaceutically acceptable salt or solvate thereof:

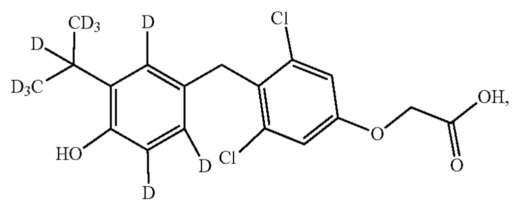

,

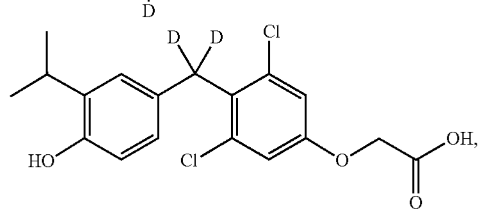

,

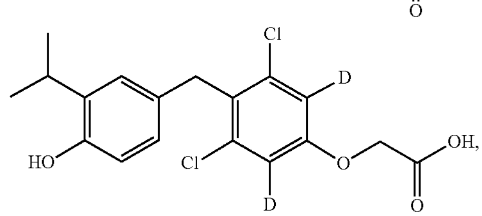

,

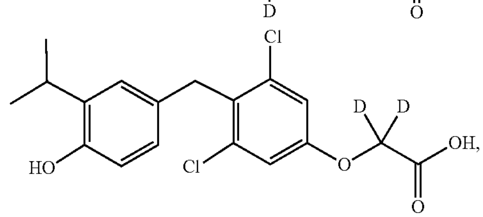

,

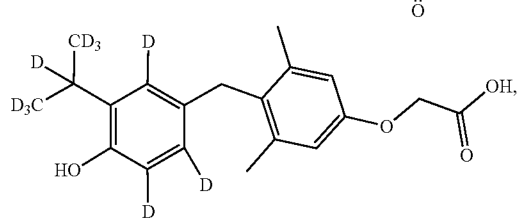

,

-continued

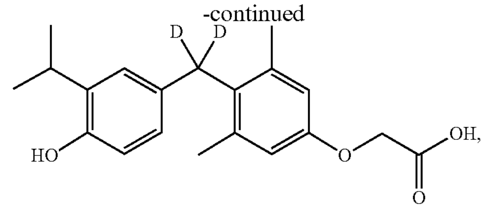

,

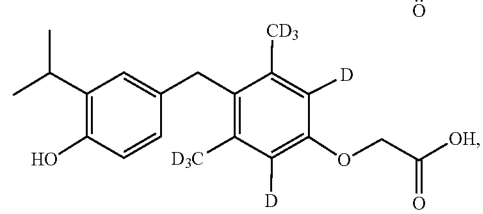

,

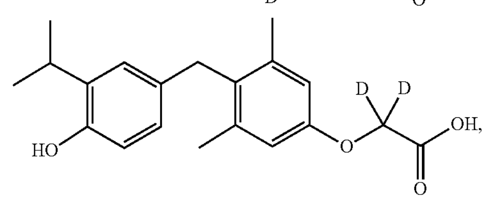

,

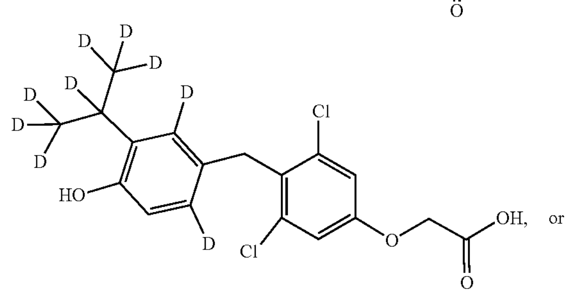

, or

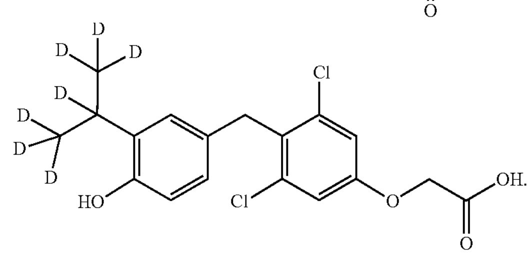

.

5. A pharmaceutical composition comprising a pharmaceutically effective amount of a compound of claim 1, or a pharmaceutically acceptable salt or solvate thereof, and one or more pharmaceutically acceptable carriers.

6. A method of treating a subject having a neurodegenerative disease, the method comprising: administering to the subject a pharmaceutically effective amount of a compound of claim 1, or a pharmaceutically acceptable salt or solvate thereof.

7. The method of claim 6, wherein the neurodegenerative disease is acute disseminated encephalomyelitis, acute hemorrhagic leukoencephalitis, adult Refsum disease, Alexander disease, Alzheimer's disease, Balo concentric sclerosis, Canavan disease, central pontine myelinolysis, cerebral palsy, cerebrotendineous xanthomatosis, chronic inflammatory demyelinating polyneuropathy, Devic's syndrome, diffuse myelinoclastic sclerosis, Guillain-Barre syndrome, idiopathic inflammatory demyelinating disease, infantile Refsum disease, Krabbe disease, Leber hereditary optic neuropathy, Marburg multiple sclerosis, Marchiafava-Bignami disease, metachromatic leukodystrophy, multifocal motor neuropathy, paraproteinemic demyelinating polyneuropathy, Pelizaeus-Merzbacher disease, peroneal muscular atrophy, progressive multifocal leukoencephalopathy, transverse myelitis, tropical spastic paraparesis, van der Knaap disease, X-linked adrenoleukodystrophy, or Zellweger syndrome.

* * * * *